(12) United States Patent
Fisher et al.

(10) Patent No.: US 7,592,295 B1
(45) Date of Patent: Sep. 22, 2009

(54) FARNESENE DIMERS AND/OR FARNESANE DIMERS AND COMPOSITIONS THEREOF

(75) Inventors: Karl Fisher, Petaluma, CA (US); Frank X. Woolard, Greenbrae, CA (US)

(73) Assignee: Amyris Biotechnologies, Inc., Emeryville, CA (US)

( * ) Notice: Subject to any disclaimer, the term of this patent is extended or adjusted under 35 U.S.C. 154(b) by 0 days.

(21) Appl. No.: 12/409,437

(22) Filed: Mar. 23, 2009

Related U.S. Application Data

(60) Provisional application No. 61/104,675, filed on Oct. 10, 2008.

(51) Int. Cl.
*C07C 13/18* (2006.01)
*C09K 8/08* (2006.01)
(52) U.S. Cl. .................................. 507/110; 585/23
(58) Field of Classification Search .............. 585/23; 507/110
See application file for complete search history.

(56) References Cited

U.S. PATENT DOCUMENTS

| | | | |
|---|---|---|---|
| 3,859,374 A | 1/1975 | Komatsu et al. | |
| 4,546,110 A | 10/1985 | Dawson et al. | |
| 6,491,809 B1 | 12/2002 | Briot et al. | |
| 7,399,323 B2 | 7/2008 | Renninger et al. | |
| 7,402,715 B2 | 7/2008 | Yoshida et al. | |
| 2005/0023188 A1 | 2/2005 | Connor | |

OTHER PUBLICATIONS

Zhang et al., *Kunchong Xuebao* (1988), 31(4), 435-8.

*Primary Examiner*—Glenn Caldarola
*Assistant Examiner*—Jim Goloboy
(74) *Attorney, Agent, or Firm*—Jones Day

(57) ABSTRACT

Farnesene dimers and/or farnesane dimers and compositions thereof are described. The compositions provided comprise conventional additives. Methods of making and using the compounds and composition are also disclosed.

20 Claims, 4 Drawing Sheets

FARNESENE DIMERS AND/OR FARNESANE DIMERS AND COMPOSITIONS THEREOF

PRIOR RELATED APPLICATIONS

This application claims the benefit under 35 U.S.C. § 119(e) of U.S. Provisional Patent Application No. 61/104,675, filed Oct. 10, 2008, incorporated herein by reference in its entirety.

FIELD

Provided herein are farnesene dimers and/or farnesane dimers and compositions comprising the same. Also provided are methods of making and using the farnesene dimers and/or farnesane dimers. In certain embodiments, the farnesene dimers and/or farnesane dimers and compositions thereof have use as lubricants, lubricity enhancers, pour point depressants or fuel additives.

BACKGROUND

Considerable effort has been expended to develop compositions for use in industrial applications associated with the automotive, tractor, airline, and railroad industries, metalworking industry and the like. There is a continuing demand for cost-effective compositions exhibiting improved characteristics.

SUMMARY

In one embodiment, provided herein are compositions comprising farnesene dimers and/or farnesane dimers. In one embodiment, provided herein are compositions comprising:

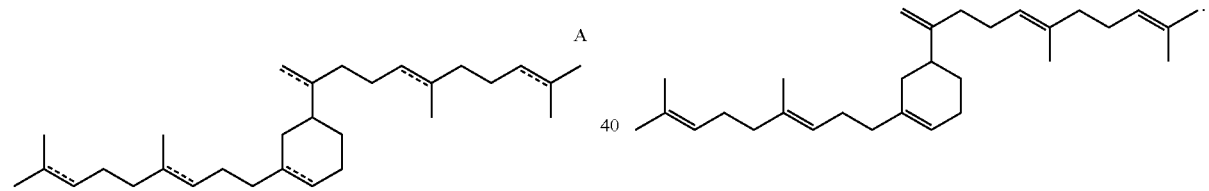

A and one or more compounds selected from:

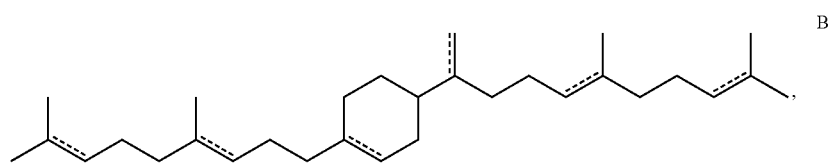

B

C

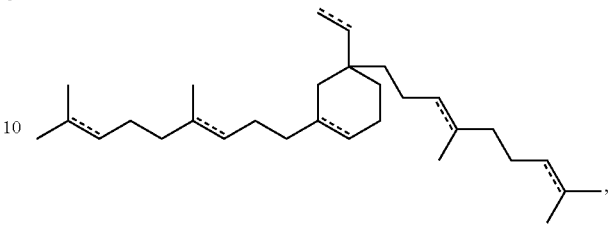

D wherein, in each compound A, B, C or D, the dual lines consisting of a solid and a broken line represent single or double bonds such that each given compound is either fully saturated or fully unsaturated. In other words, in a given compound A, B, C or D, when one dual line represents a single bond then all dual lines in that compound represent single bonds. When one dual line in a given compound A, B, C or D represents a double bond then all dual lines in that compound represent double bonds.

In one embodiment, compound A is

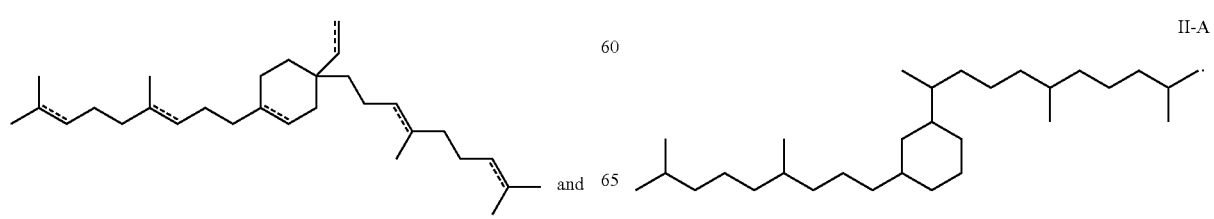

I-A

In one embodiment, compound A is

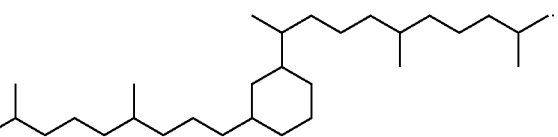

II-A

In one embodiment the one or more compounds are selected from:
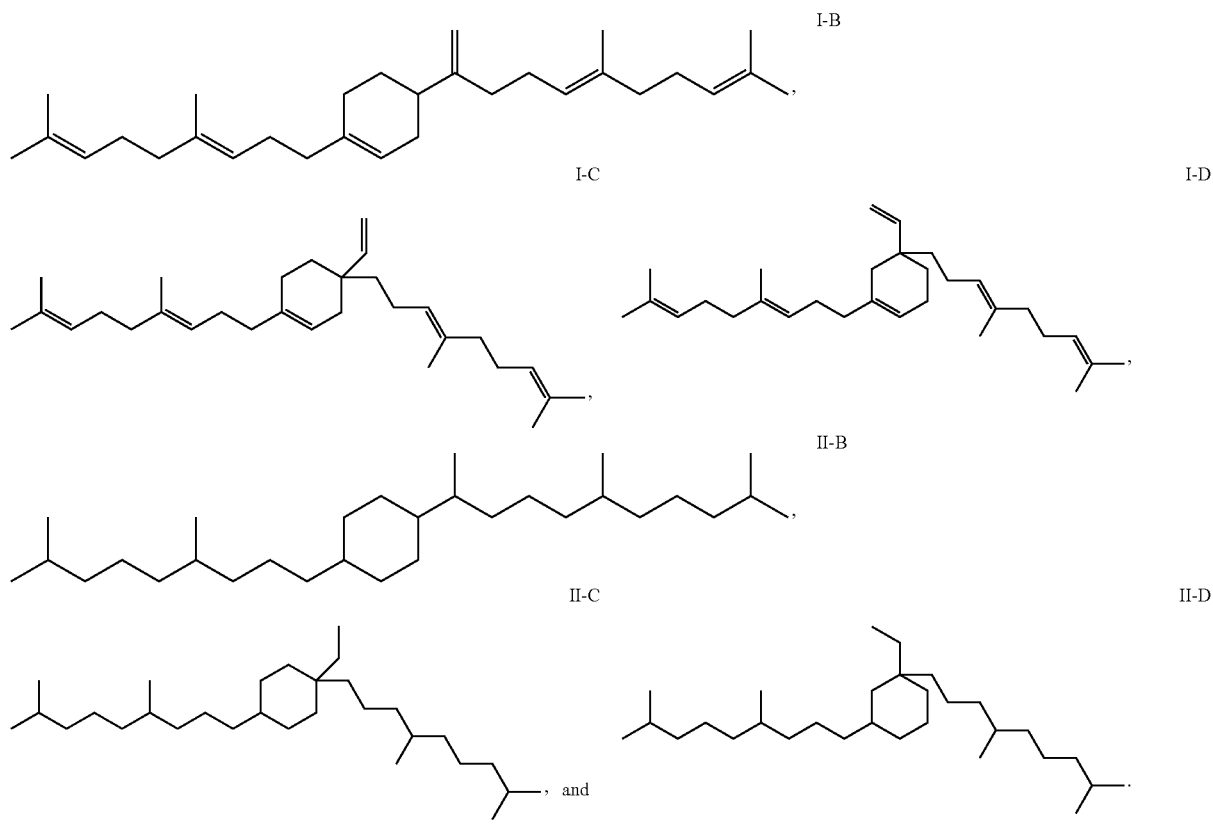
In another embodiment, the compositions comprise two or more compounds selected from:
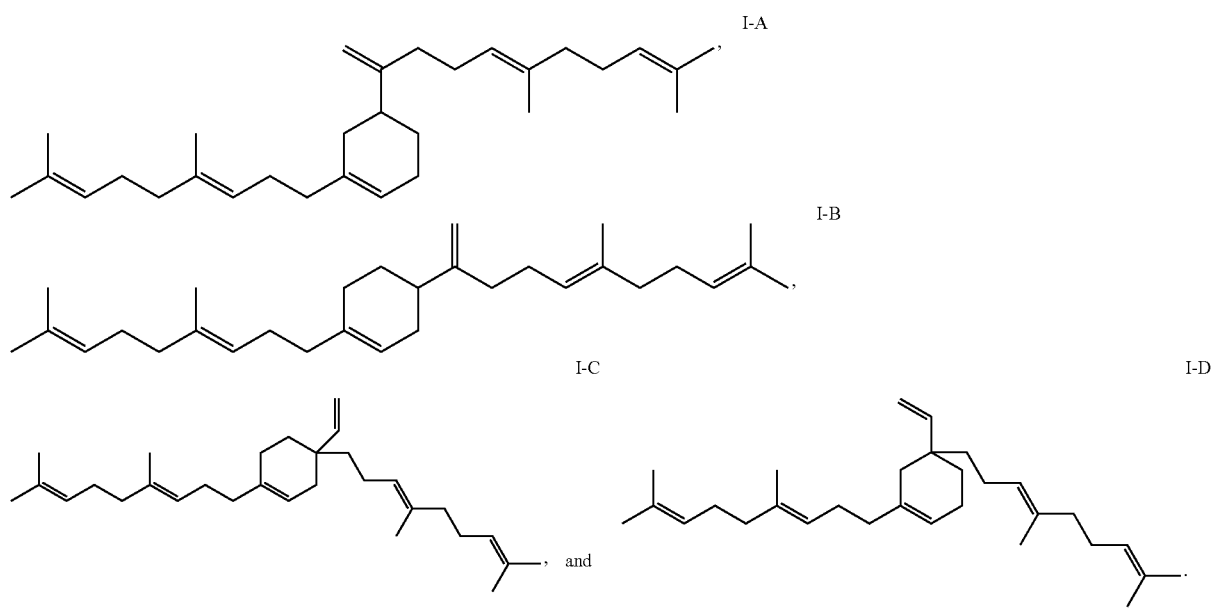

In another embodiment, the compositions comprise two or more compounds selected from:

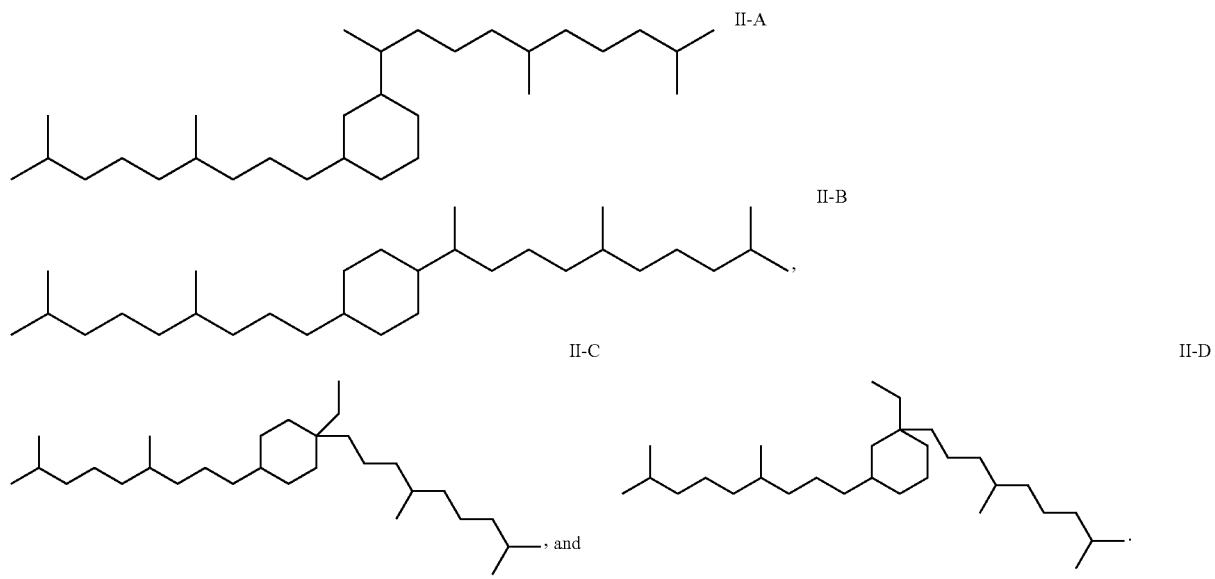

In one embodiment, compositions provided herein comprise farnesene dimers of formulas I-A and I-B. In another embodiment, compositions comprise farnesene dimers of formulas I-A, I-B, I-C and I-D. In another embodiment, compositions provided herein comprise farnesane dimers of formulas II-A, II-B, II-C and II-D. In one embodiment, compositions provided herein comprise farnesane dimers of formulas II-A and II-B. In another embodiment, compositions provided herein comprise farnesene dimers and/or farnesane dimers of formulas I-A, I-B, I-C, I-D, II-A, II-B, II-C, II-D or a mixture thereof.

In certain embodiments, said compositions are lubricant compositions. In one embodiment, the lubricant compositions provided herein comprise farnesene dimers of formulas I-A and I-B. In another embodiment, the lubricant compositions comprise farnesene dimers of formulas I-A, I-B, I-C and I-D. In another embodiment, the lubricant compositions comprise farnesane dimers of formulas II-A, II-B, II-C and II-D. In one embodiment, the lubricant compositions provided herein comprise farnesane dimers of formulas II-A and II-B. In another embodiment, the lubricant compositions comprise farnesene dimers and/or farnesane dimers of formulas I-A, I-B, I-C, I-D, II-A, II-B, II-C and II-D.

In certain embodiments, compositions provided herein have a viscosity index greater than about 200 according to ASTM D 2270. In certain embodiments, the viscosity index is from about 230 to about 240 according to ASTM D 2270. The compositions provided herein can exist as liquid compositions at room temperature.

In certain embodiments, provided herein is a compound selected from the group consisting of:

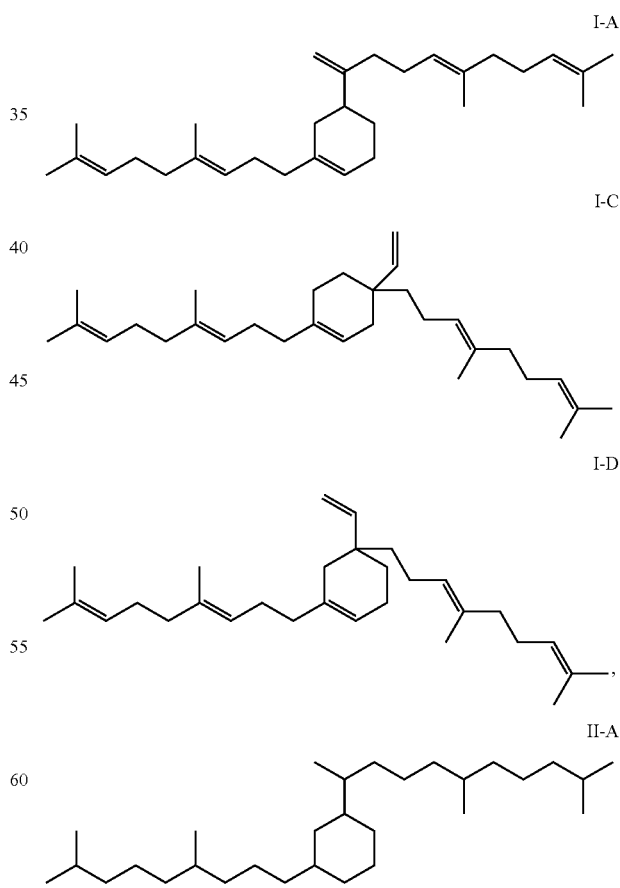

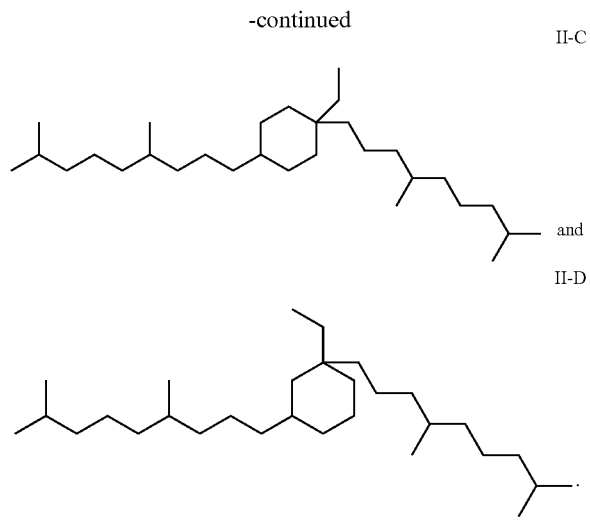

In certain embodiments, provided herein is a composition comprising compounds I-A and I-B. In certain embodiments, the composition further comprises compounds I-C and I-D. In certain embodiments, provided herein is a composition comprising compounds II-A and II-B. In certain embodiments, the composition further comprises compounds II-C and II-D.

In certain embodiments, the farnesene dimers and/or farnesane dimers and compositions thereof have utility as lubricity enhancers, pour point depressants and/or fuel additives. The farnesene dimers and/or farnesane dimers and compositions thereof can be used in a wide variety of applications, including but not limited to, applications associated with the automotive, tractor, airline, and railroad industries including engines, transmissions, and the like, metal-working fluids, quench fluids, greases, crankcase lubricants, power transmission fluids, vehicle axle applications, hydraulic systems, heavy duty gear oils, and rotating machinery such as stationary engines, pumps, gas turbines, compressors, wind turbines, and the like. Stationary engines include fuel and gas powered engines that are not associated with the automotive, tractor, airline, and railroad industries. Also provided are methods of making the compounds and compositions.

In certain embodiments, compositions provided herein are readily biodegradable. In certain embodiments, compositions provided herein are low in toxicity and pose little or no harm to aquatic organisms or surrounding vegetation. These qualities are particularly useful for applications in environmentally sensitive areas such as marine ecosystems, and for those with a high potential of being lost to the surrounding environment. In certain embodiments, compositions provided herein can be derived from readily available, renewable materials.

In certain embodiments, provided herein is a method of lubricating a machine by operating the machine in contact with a composition provided herein. The compositions can be used for lubricating any machine that needs lubrication. Exemplary machines include, but are not limited to engines, pumps, gas turbines, compressors, wind turbines, and the like. In certain embodiments, the engine is a fuel and/or gas powered engine associated with the automotive, tractor, airline, and railroad industries. In certain embodiments, the engine is a stationary engine, including a fuel and/or gas powered engine that is not associated with the automotive, tractor, airline, and railroad industries.

In certain embodiments, provided herein is a machine comprising a composition provided herein.

DEFINITIONS

Figure 1:
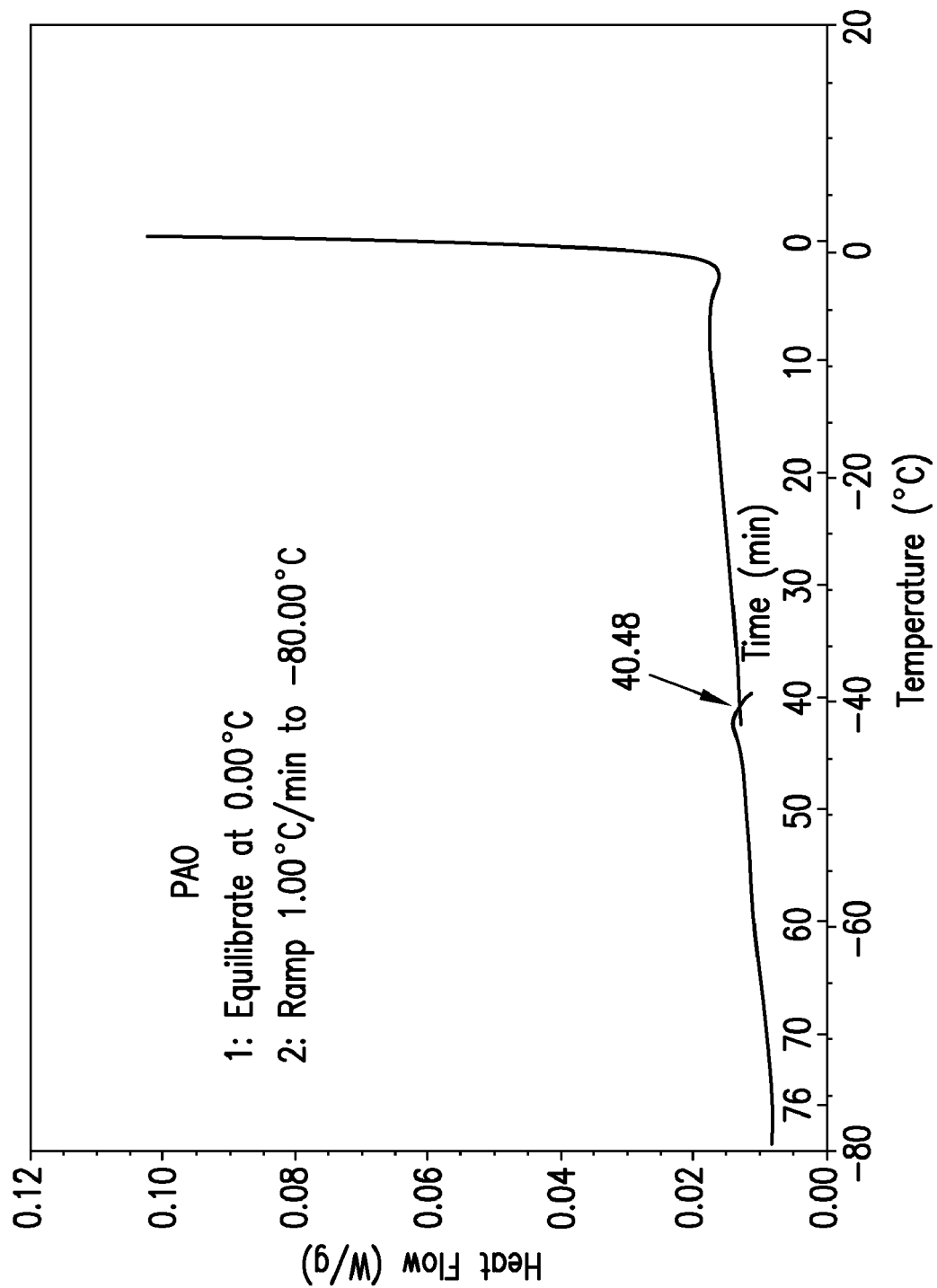
FIG. 1 depicts the differential scanning calorimetry (DSC) plot for compositions comprising poly alpha olefins (PAO).

In the following description, all numbers disclosed herein are approximate values, regardless whether the word "about" or "approximate" is used in connection therewith. Numbers may vary by 1 percent, 2 percent, 5 percent, or, sometimes, 10 to 20 percent. Whenever a numerical range with a lower limit, $R^L$, and an upper limit, $R^U$, is disclosed, any number falling within the range is specifically disclosed. In particular, the following numbers within the range are specifically disclosed: $R=R^L+k*(R^U-R^L)$, wherein k is a variable ranging from 1 percent to 100 percent with a 1 percent increment, i.e., k is 1 percent, 2 percent, 3 percent, 4 percent, 5 percent, ..., 50 percent, 51 percent, 52 percent, ..., 95 percent, 96 percent, 97 percent, 98 percent, 99 percent, or 100 percent. Moreover, any numerical range defined by two R numbers as defined in the above is also specifically disclosed.

As used herein, "β-Farnesene" refers to a compound having the following formula:

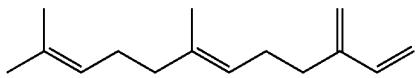

or a stereoisomer thereof. In some embodiments, the β-farnesene comprises a substantially pure stereoisomer of β-farnesene. In other embodiments, the β-farnesene comprises a mixture of stereoisomers, such as cis-trans isomers. In further embodiments, the amount of each of the stereoisomers in the β-farnesene mixture is independently from about 0.1 wt. % to about 99.9 wt. %, from about 0.5 wt. % to about 99.5 wt. %, from about 1 wt. % to about 99 wt. %, from about 5 wt. % to about 95 wt. %, from about 10 wt. % to about 90 wt. %, from about 20 wt. % to about 80 wt. %, based on the total weight of the β-farnesene mixture.

DESCRIPTION OF EMBODIMENTS

In one embodiment, provided herein are compositions comprising two or more farnesene dimers and/or farnesane dimers.

In one embodiment, provided herein are compositions comprising:

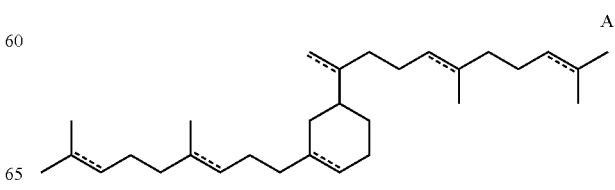

and one or more compounds selected from:

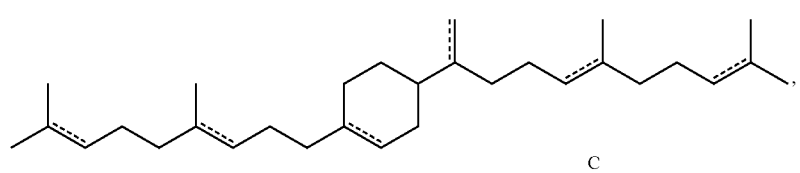
B

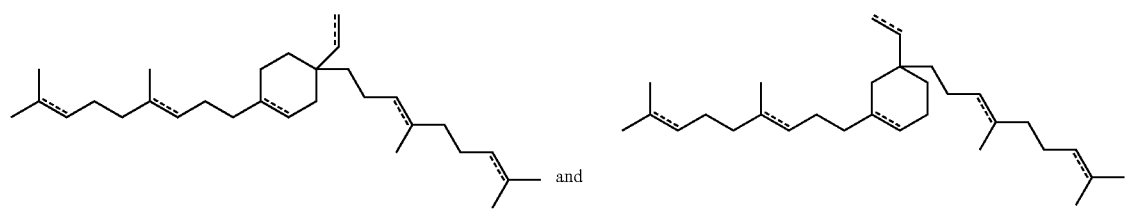
C

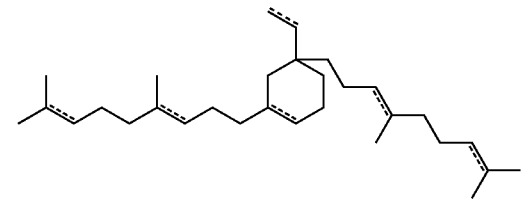
D and such that in a given compound A, B, C or D, when one dual line represents a single bond then all dual lines in that compound represent single bonds. When one dual line in a given compound A, B, C or D represents a double bond then all dual lines in that compound represent double bonds. In other words, in each compound A, B, C or D the dual lines consisting of a solid and a broken line represent a single or a double bonds such that each given compound is either fully saturated or fully unsaturated.

In one embodiment, compound A is

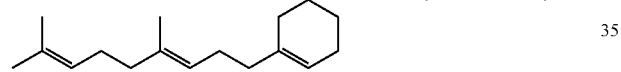
I-A

In one embodiment, compound A is

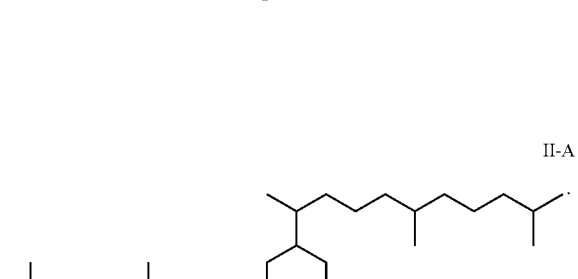
II-A

In one embodiment, the one or more compounds are selected from:

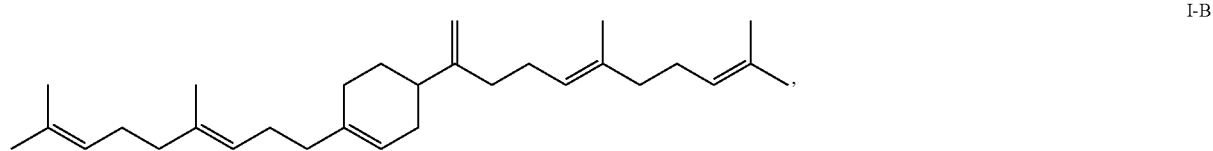
I-B

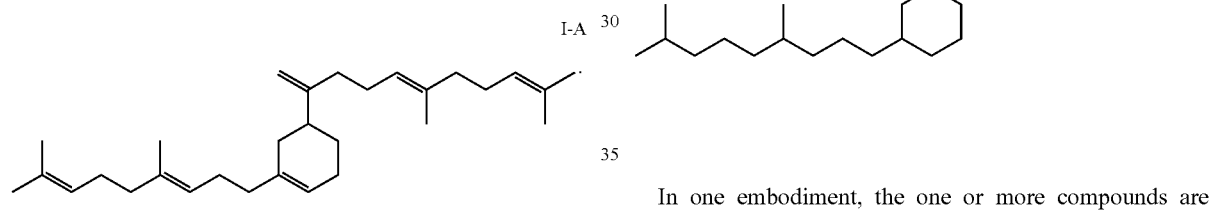
I-C

I-D

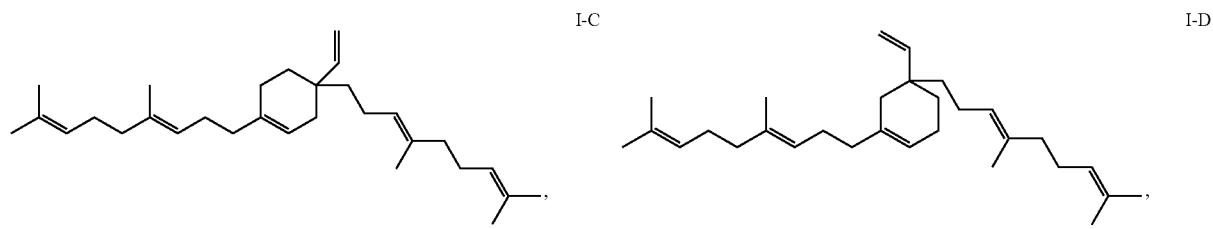

II-B

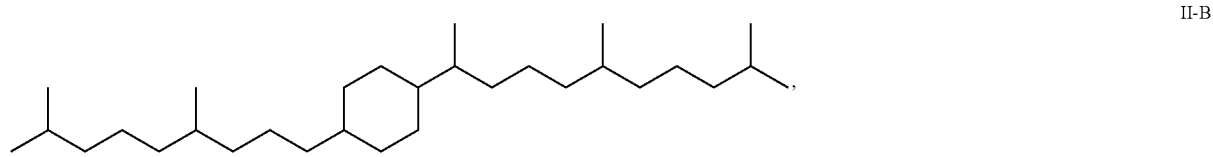

-continued
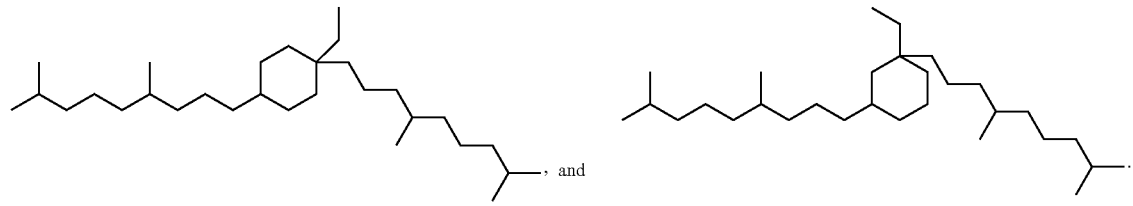
In another embodiment, the compositions comprise two or more compounds selected from:
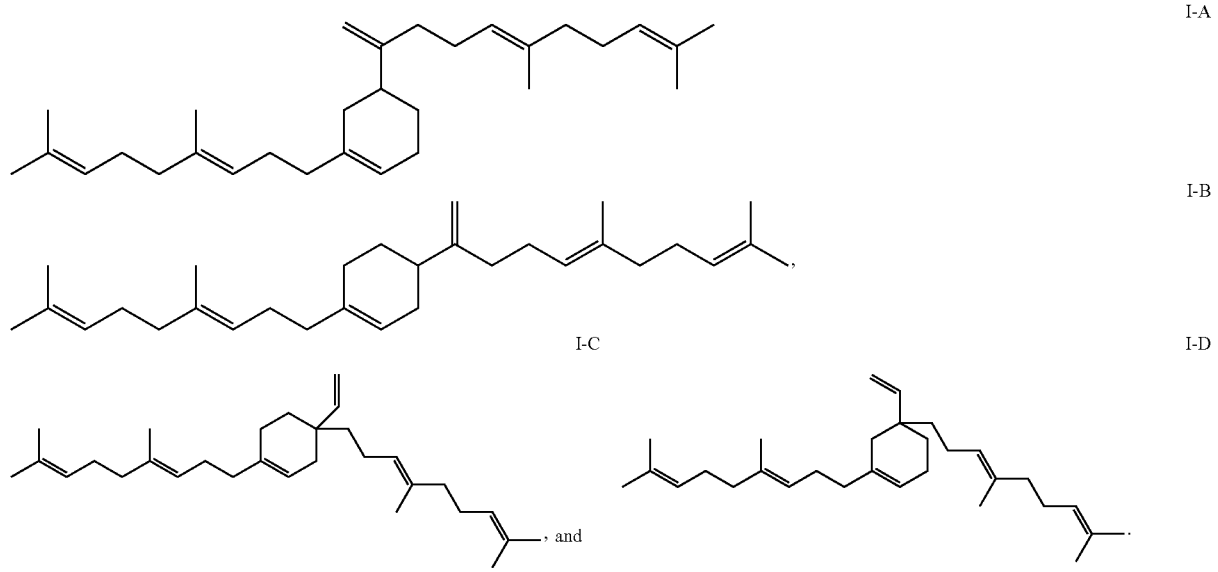
In another embodiment, the compositions comprise two or more compounds selected from:
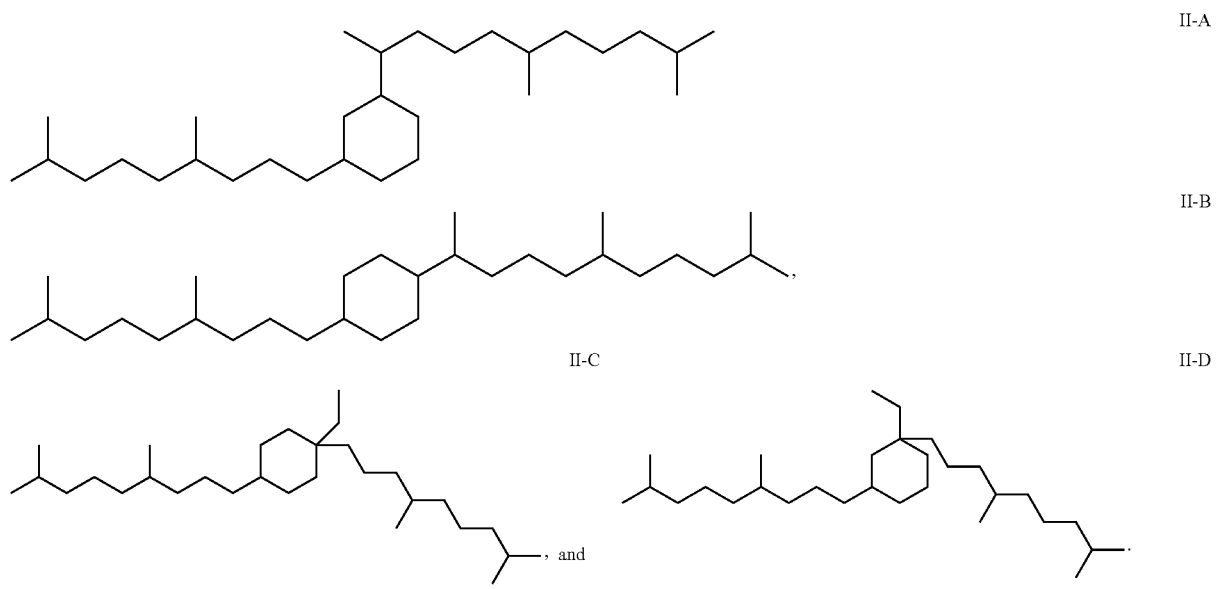

In one embodiment, compositions provided herein comprise farnesene dimers of formulas I-A and I-B. In another embodiment, compositions provided herein comprise farnesene dimers of formulas I-A, I-B, I-C and I-D.

In another embodiment, compositions provided herein comprise farnesane dimers of formulas II-A, II-B, II-C and II-D. In one embodiment, compositions provided herein comprise farnesane dimers of formulas II-A and II-B. In another embodiment, compositions provided herein comprise farnesene dimers and/or farnesane dimers of formulas I-A, I-B, I-C, I-D, II-A, II-B, II-C and II-D.

In certain embodiments, the amount of one or more farnesene dimers and/or farnesane dimers in compositions provided herein is at least about 0.1% based on the total weight of the composition. In certain embodiments, the amount of one or more farnesene dimers and/or farnesane dimers in compositions provided herein is from about 1 to about 95% based on the total weight of the composition. In certain embodiments, the amount of one or more farnesene dimers and/or farnesane dimers in compositions provided herein is at least about 0.1, 1, 2, 3, 4, 5, 7, 9, 10, 15, 20, 25, 30, 35, 40, 45, 50, 60, 70, 80, 90, 92, 95, 96, 97, 98, 99 or 99.5% based on the total weight of the composition.

In certain embodiments, the amount of farnesene dimer of formula I-A in compositions provided herein is at least about 10% based on the total weight of the farnesene dimers. In certain embodiments, the amount of farnesene dimer of formula I-A in compositions provided herein is at least about 20% based on the total weight of the farnesene dimers. In certain embodiments, the amount of farnesene dimer of formula I-A in compositions provided herein is from about 25 to about 90%, about 25 to about 80%, about 30 to about 70%, about 30 to about 60%, about 30 to about 50% or about 30 to about 40% based on the total weight of the farnesene dimers in the composition. In certain embodiments, the amount of farnesene dimer of formula I-A in the compositions is at least about 5, 10, 12, 14, 15, 17, 20, 25, 30, 35, 37, 40, 50, 60, 70, 75, 80 or 90% based on the total weight of the farnesene dimers in the composition. In certain embodiments, the amount of farnesene dimer of formula I-A in the compositions is at least about 25, 30, 35, 40, 50, 60, 70, 75, 80 or 90% based on the total weight of the farnesene dimers in the composition.

In certain embodiments, the amount of farnesene dimer of formula I-B in compositions provided herein is at least about 10% based on the total weight of the farnesene dimers. In certain embodiments, the amount of farnesene dimer of formula I-B in compositions provided herein is at least about 20% based on the total weight of the farnesene dimers in the composition. In certain embodiments, the amount of farnesene dimer of formula I-B in compositions provided herein is at least about 25% based on the total weight of the farnesene dimers in the composition. In certain embodiments, the amount of farnesene dimer of formula I-B in compositions provided herein is from about 25 to about 90%, about 25 to about 80%, about 30 to about 70%, about 30 to about 60%, about 30 to about 50% or about 30 to about 40% based on the total weight of the farnesene dimers in the composition. In certain embodiments, the amount of farnesene dimer of formula I-B in the compositions is at least about 5, 10, 12, 14, 15, 17, 20, 25, 30, 35, 37, 40, 50, 60, 70, 75, 80 or 90% based on the total weight of the farnesene dimers in the composition. In certain embodiments, the amount of farnesene dimer of formula I-B in compositions provided herein is at least about 25, 30, 35, 40, 50, 60, 70, 75, 80 or 90% based on the total weight of the farnesene dimers in the composition.

In certain embodiments, the amount of farnesene dimer of formula I-C in compositions provided herein is at least about 1% or about 2% based on the total weight of the farnesene dimers in the composition. In certain embodiments, the amount of farnesene dimer of formula I-C in compositions provided herein is at least about 5% based on the total weight of the farnesene dimers in the composition. In certain embodiments, the amount of farnesene dimer of formula I-C in compositions provided herein is from about 5 to about 40%, about 5 to about 30%, about 10 to about 25% or about 10 to about 20% based on the total weight of the farnesene dimers in the composition. In certain embodiments, the amount of farnesene dimer of formula I-C in compositions provided herein is at least about 1, 2, 3, 4, 5, 6, 7, 8, 9, 10, 11, 12, 15, 20, 25, 30, 35 or 40% based on the total weight of the farnesene dimers in the composition. In certain embodiments, the amount of farnesene dimer of formula I-C in compositions provided herein is at least about 5, 10, 12, 15, 20, 25, 30, 35 or 40% based on the total weight of the farnesene dimers in the composition.

In certain embodiments, the amount of farnesene dimer of formula I-D in compositions provided herein is at least about 1% or about 2% based on the total weight of the farnesene dimers in the composition. In certain embodiments, the amount of farnesene dimer of formula I-D in compositions provided herein is at least about 5% based on the total weight of the farnesene dimers in the composition. In certain embodiments, the amount of farnesene dimer of formula I-D in compositions provided herein is from about 5 to about 40%, about 5 to about 30%, about 10 to about 25% or about 10 to about 20% based on the total weight of the farnesene dimers in the composition. In certain embodiments, the amount of farnesene dimer of formula I-D in compositions provided herein is at least about 1, 2, 3, 4, 5, 6, 7, 8, 9, 10, 11, 12, 15, 20, 25, 30, 35 or 40% based on the total weight of the farnesene dimers in the composition. In certain embodiments, the amount of farnesene dimer of formula I-D in compositions provided herein is at least about 5, 10, 12, 15, 20, 25, 30, 35 or 40% based on the total weight of the farnesene dimers in the composition.

In certain embodiments, the total amount of farnesene dimers of formulas I-A and I-B in compositions provided herein is at least about 10% based on the total weight of the farnesene dimers in the composition. In certain embodiments, the total amount of farnesene dimers of formulas I-A and I-B in compositions provided herein is at least about 20% based on the total weight of the farnesene dimers in the composition. In certain embodiments, the total amount of farnesene dimers of formulas I-A and I-B in compositions provided herein is at least about 40% based on the total weight of the farnesene dimers in the composition. In certain embodiments, the total amount of farnesene dimers of formulas I-A and I-B in compositions provided herein is from about 40 to about 90%, about 50 to about 85%, about 50 to about 80% or about 60 to about 80% based on the total weight of the farnesene dimers in the composition. In certain embodiments, the total amount of farnesene dimers of formulas I-A and I-B in compositions provided herein is at least about 5, 10, 15, 20, 25, 30, 35, 37, 40, 45, 50, 60, 70, 75, 80 or 90% based on the total weight of the farnesene dimers in the composition. In certain embodiments, the total amount of farnesene dimers of formulas I-A and I-C in compositions provided herein is at least about 40, 50, 60, 70, 75, 80 or 90% based on the total weight of the farnesene dimers in the composition.

In certain embodiments, the total amount of farnesene dimers of formulas I-C and I-D in compositions provided herein is at least about 1%, 2%, 3%, 4%, 5%, 6%, 7%, 8%, 9%, 10%, 11% or 12% based on the total weight of the farnesene dimers in the composition. In certain embodiments, the total amount of farnesene dimers of formulas I-C and I-D in compositions provided herein is at least about 10% based on the total weight of the farnesene dimers in the composition. In certain embodiments, the total amount of farnesene dimers of formulas I-C and I-D in compositions provided herein is from about 10 to about 40%, about 10 to about 30%, about 10 to about 25% or about 10 to about 20% based on the total weight of the farnesene dimers in the composition. In certain embodiments, the total amount of farnesene dimers of formulas I-C and I-D in compositions provided herein is at least about 10, 15, 20, 25, 30, 35 or 40% based on the total weight of the farnesene dimers in the composition.

In certain embodiments, the amount of farnesane dimer of formula II-A in compositions provided herein is at least about 10% based on the total weight of the farnesane dimers in the composition. In certain embodiments, the amount of farnesane dimer of formula II-A in compositions provided herein is at least about 20% based on the total weight of the farnesane dimers in the composition. In certain embodiments, the amount of farnesane dimer of formula II-A in compositions provided herein is at least about 25% based on the total weight of the farnesane dimers in the composition. In certain embodiments, the amount of farnesane dimer of formula II-A in compositions provided herein is from about 25 to about 90%, about 25 to about 80%, about 30 to about 70%, about 30 to about 60%, about 30 to about 50% or about 30 to about 40% based on the total weight of the farnesane dimers in the composition. In certain embodiments, the amount of farnesene dimer of formula II-A in the compositions is at least about 5, 10, 12, 14, 15, 17, 20, 25, 30, 35, 37, 40, 45, 50, 60, 70, 75, 80 or 90% based on the total weight of the farnesene dimers in the composition. In certain embodiments, the amount of farnesane dimer of formula II-A in compositions provided herein is at least about 25, 30, 35, 40, 50, 60, 70, 75, 80 or 90% based on the total weight of the farnesane dimers in the composition.

In certain embodiments, the amount of farnesane dimer of formula II-B in compositions provided herein is at least about 20% based on the total weight of the farnesane dimers in the composition. In certain embodiments, the amount of farnesane dimer of formula II-B in compositions provided herein is at least about 25% based on the total weight of the farnesane dimers in the composition. In certain embodiments, the amount of farnesane dimer of formula II-B in compositions provided herein is from about 25 to about 90%, about 25 to about 80%, about 30 to about 70%, about 30 to about 60%, about 30 to about 50% or about 30 to about 40% based on the total weight of the farnesane dimers in the composition. In certain embodiments, the amount of farnesene dimer of formula II-B in the compositions is at least about 10, 12, 14, 15, 17, 20, 25, 30, 35, 37, 40, 45, 50, 60, 70, 75, 80 or 90% based on the total weight of the farnesene dimers in the composition. In certain embodiments, the amount of farnesane dimer of formula II-B in compositions provided herein is at least about 25, 30, 35, 40, 50, 60, 70, 75, 80 or 90% based on the total weight of the farnesane dimers in the composition.

In certain embodiments, the amount of farnesane dimer of formula II-C in compositions provided herein is at least about 5% based on the total weight of the farnesane dimers in the composition. In certain embodiments, the amount of farnesane dimer of formula II-C in compositions provided herein is from about 5 to about 40%, about 5 to about 30%, about 10 to about 25% or about 10 to about 20% based on the total weight of the farnesane dimers in the composition. In certain embodiments, the amount of farnesene dimer of formula II-C in compositions provided herein is at least about 1, 2, 3, 4, 5, 6, 7, 8, 9, 10, 11, 12, 15, 20, 25, 30, 35 or 40% based on the total weight of the farnesene dimers in the composition. In certain embodiments, the amount of farnesane dimer of formula II-C in compositions provided herein is at least about 5, 10, 12, 15, 20, 25, 30, 35 or 40% based on the total weight of the farnesane dimers in the composition.

In certain embodiments, the amount of farnesane dimer of formula II-D in compositions provided herein is at least about 5% based on the total weight of the farnesane dimers in the composition. In certain embodiments, the amount of farnesane dimer of formula II-D in compositions provided herein is from about 5 to about 40%, about 5 to about 30%, about 10 to about 25% or about 10 to about 20% based on the total weight of the farnesane dimers in the composition. In certain embodiments, the amount of farnesene dimer of formula II-D in compositions provided herein is at least about 1, 2, 3, 4, 5, 6, 7, 8, 9, 10, 11, 12, 15, 20, 25, 30, 35 or 40% based on the total weight of the farnesene dimers in the composition. In certain embodiments, the amount of farnesane dimer of formula II-D in compositions provided herein is at least about 5, 10, 12, 15, 20, 25, 30, 35 or 40% based on the total weight of the farnesane dimers in the composition.

In certain embodiments, the total amount of farnesane dimers of formula II-A and II-B in compositions provided herein is at least about 40% based on the total weight of the farnesane dimers in the composition. In certain embodiments, the total amount of farnesane dimers of formulas II-A and II-B in compositions provided herein is from about 40 to about 99.5%, about 50 to about 90%, about 50 to about 85% or about 60 to about 80% based on the total weight of the farnesane dimers in the composition. In certain embodiments, the total amount of farnesene dimers of formulas II-A and II-B in compositions provided herein is at least about 10, 15, 20, 25, 30, 35, 37, 40, 45, 50, 60, 70, 75, 80 or 90% based on the total weight of the farnesene dimers in the composition. In certain embodiments, the total amount of farnesane dimers of formulas II-A and II-B in compositions provided herein is at least about 40, 50, 60, 70, 75, 80 or 90% based on the total weight of the farnesane dimers in the composition.

In certain embodiments, the total amount of farnesene dimers of formulas II-C and II-D in compositions provided herein is at least about 1%, 2%, 3%, 4%, 5%, 6%, 7%, 8%, 9%, 10%, 11% or 12% based on the total weight of the farnesene dimers in the composition. In certain embodiments, the total amount of farnesene dimers of formulas II-C and II-D in compositions provided herein is at least about 10% based on the total weight of the farnesane dimers in the composition. In certain embodiments, the total amount of farnesane dimers of formula II-C and II-D in compositions provided herein is from about 10 to about 40%, about 10 to about 30%, about 10 to about 25% or about 10 to about 20% based on the total weight of the farnesane dimers in the composition. In certain embodiments, the total amount of farnesane dimers of formula II-C and II-D in compositions provided herein is at least about 10, 15, 20, 25, 30, 35 or 40% based on the total weight of the farnesane dimers in the composition.

In certain embodiments, compositions provided herein comprise farnesene dimers of formulas I-A, I-B, I-C and I-D. In one embodiment, the amount of farnesene dimer of formula I-A in compositions provided herein is at least about 10%, the amount of farnesene dimer of formula I-B in compositions provided herein is at least about 10%, the amount of farnesene dimer of formula I-C in compositions provided herein is at least about 1% and the amount of farnesene dimer of formula I-D in compositions provided herein is at least about 1% based on the total weight of the farnesene dimers in the composition. In one embodiment, the amount of farnesene dimer of formula I-A in compositions provided herein is at least about 20%, the amount of farnesene dimer of formula I-B in compositions provided herein is at least about 20%, the amount of farnesene dimer of formula I-C in compositions provided herein is at least about 2% and the amount of farnesene dimer of formula I-D in compositions provided herein is at least about 2% based on the total weight of the farnesene dimers in the composition. In one embodiment, the amount of farnesene dimer of formula I-A in compositions provided herein is at least about 30%, the amount of farnesene dimer of formula I-B in compositions provided herein is at least about 30%, the amount of farnesene dimer of formula I-C in compositions provided herein is at least about 5% and the amount of farnesene dimer of formula I-D in compositions provided herein is at least about 5% based on the total weight of the farnesene dimers in the composition. In one embodiment, the amount of farnesene dimer of formula I-A in compositions provided herein is from about 30% to about 50%, the amount of farnesene dimer of formula I-B in compositions provided herein is from about 30% to about 50%, the amount of farnesene dimer of formula I-C in compositions provided herein is from about 5% to about 15% and the amount of farnesene dimer of formula I-D in compositions provided herein is from about 5% to about 15% based on the total weight of the farnesene dimers in the composition. In one embodiment, compositions provided herein comprise farnesene dimer of formula I-A in about 40%, farnesene dimer of formula I-B in about 40%, farnesene dimer of formula I-C in about 10%, and farnesene dimer of formula I-D in about 10% based on the total weight of the farnesene dimers in the composition.

In certain embodiments, the compositions provided herein comprise farnesane dimers of formula II-A, II-B, II-C and II-D. In one embodiment, the amount of farnesane dimer of formula II-A in compositions provided herein is at least about 10%, the amount of farnesane dimer of formula II-B in compositions provided herein is at least about 10%, the amount of farnesane dimer of formula II-C in compositions provided herein is at least about 1% and the amount of farnesane dimer of formula II-D in compositions provided herein is at least about 1% based on the total weight of the farnesane dimers in the composition. In one embodiment, the amount of farnesane dimer of formula II-A in compositions provided herein is at least about 20%, the amount of farnesane dimer of formula II-B in compositions provided herein is at least about 20%, the amount of farnesane dimer of formula II-C in compositions provided herein is at least about 2% and the amount of farnesane dimer of formula II-D in compositions provided herein is at least about 2% based on the total weight of the farnesane dimers in the composition. In one embodiment, the amount of farnesane dimer of formula II-A in compositions provided herein is at least about 30%, the amount of farnesane dimer of formula II-B in compositions provided herein is at least about 30%, the amount of farnesane dimer of formula II-C in compositions provided herein is at least about 5% and the amount of farnesane dimer of formula II-D in compositions provided herein is at least about 5% based on the total weight of the farnesane dimers in the composition. In one embodiment, the amount of farnesane dimer of formula II-A in compositions provided herein is from about 30% to about 50%, the amount of farnesane dimer of formula II-B in compositions provided herein is from about 30% to about 50%, the amount of farnesane dimer of formula II-C in compositions provided herein is from about 5% to about 15% and the amount of farnesane dimer of formula II-D in compositions provided herein is from about 5% to about 15% based on the total weight of the farnesane dimers in the composition. In one embodiment, compositions provided herein comprise farnesane dimer of formula II-A in about 40%, farnesane dimer of formula II-B in about 40%, farnesane dimer of formula II-C in about 10%, and farnesane dimer of formula II-D in about 10% based on the total weight of the farnesane dimers in the composition.

In certain embodiments, compositions provided herein comprise farnesene dimers of formula I-A:I-B:I-C:I-D in a ratio of 4:4:1:1. In certain embodiments, compositions provided herein comprise farnesane dimers of formula II-A:II-B:II-C:II-D in a ratio of 4:4:1:1.

In certain embodiments, the compounds and compositions provided herein have viscosity at 100° C. from about 5 centistokes (cSt) to about 20 cSt, from about 5 centistokes (cSt) to about 15 cSt, or from about 7 cSt to about 13 cSt. In certain embodiments, the compounds and compositions have viscosity of about 10 cSt at 100° C. In certain embodiments, the compounds and compositions provided herein have viscosity at 40° C. from about 25 centistokes (cSt) to about 50 cSt, from about 30 centistokes (cSt) to about 50 cSt, or from about 35 cSt to about 45 cSt. In certain embodiments, the compounds and compositions have viscosity of about 43 cSt at 40° C. The viscosity of the compounds and compositions disclosed herein can be measured according to ASTM D 445.

In certain embodiments, the compounds and compositions provided herein have a viscosity index greater than about 200 according to ASTM D 2270. In certain embodiments, the viscosity index is greater than about 220 according to ASTM D 2270. In certain embodiments, the viscosity index is from about 220 to about 245 according to ASTM D 2270. In certain embodiments, the viscosity index is from about 230 to about 240 according to ASTM D 2270.

In certain embodiments, provided herein are lubricant compositions comprising one or more compounds of formula I-A, I-B, I-C, I-D, II-A, II-B, II-C, and II-D. The lubricant compositions provided herein may further comprise a base oil and/or a suitable lubricating oil additive.

In certain embodiments, the compounds and compositions provided herein have use as lubricity enhancers. In another embodiment, provided herein are lubricity enhancer compositions comprising one or more compounds of formula I-A, I-B, I-C, I-D, II-A, II-B, II-C, and II-D and a suitable lubricating oil additive. In certain embodiments, the lubricity enhancer compositions comprise between 0.1 and 75%, between 1 and 65%, or between 5 and 50% of the compound of formula I-A, I-B, I-C, I-D, II-A, II-B, II-C, II-D or a combination thereof. Any lubricating oil additive known to a person of ordinary skill in the art may be used in the lubricity enhancer compositions disclosed herein. In some embodiments, the lubricating oil additive can be selected from the group consisting of antioxidants, antiwear agents, detergents, rust inhibitors, demulsifiers, friction modifiers, multi-functional additives, pour point depressants, foam inhibitors, metal deactivators, dispersants, corrosion inhibitors, thermal stability improvers, dyes, markers, and combinations thereof.

In another embodiment, provided herein are lubricity enhancer compositions comprising a compound of formula I-A, I-B, I-C, I-D, II-A, II-B, II-C, II-D or a combination thereof, a suitable additive and optionally a base oil of lubricating viscosity.

Any base oil known to a skilled artisan can be used as the oil of lubricating viscosity disclosed herein. Some base oils suitable for preparing the lubricant compositions have been described in Mortier et al., "*Chemistry and Technology of Lubricants,*" 2nd Edition, London, Springer, Chapters 1 and 2 (1996); and A. Sequeria, Jr., "*Lubricant Base Oil and Wax*

Processing," New York, Marcel Decker, Chapter 6, (1994); and D. V. Brock, *Lubrication Engineering*, Vol. 43, pages 184-5, (1987), all of which are incorporated herein by reference. In certain embodiments, the amount of the base oil in the composition is greater than about 1% based on the total weight of the composition. In certain embodiments, the amount of the base oil in the composition is greater that about 2, 5, 15 or 20% based on the total weight of the composition. In some embodiments, the amount of the base oil in the composition is from about 1-20% based on the total weight of the composition. In certain embodiments, the amount of base oil in compositions provided herein is about 1%, 5%, 7%, 10%, 13%, 15%, or 20% based on total weight of the composition.

In certain embodiments, the base oil is or comprises any natural or synthetic lubricating base oil fraction. Some non-limiting examples of synthetic oils include oils, such as poly-alphaolefins or PAOs, prepared from the polymerization of at least one alpha-olefin, such as ethylene, or from hydrocarbon synthesis procedures using carbon monoxide and hydrogen gases, such as the Fisher-Tropsch process.

In other embodiments, the base oil is or comprises a base stock or blend of base stocks. In further embodiments, the base stocks are manufactured using a variety of different processes including, but not limited to, distillation, solvent refining, hydrogen processing, oligomerization, esterification, and rerefining. In some embodiments, the base stocks comprise a rerefined stock. In further embodiments, the rerefined stock is substantially free from materials introduced through manufacturing, contamination, or previous use.

In some embodiments, the base oil comprises one or more of the base stocks in one or more of Groups I-V as specified in the American Petroleum Institute (API) Publication 1509, Fourteen Edition, December 1996 (i.e., API Base Oil Interchangeability Guidelines for Passenger Car Motor Oils and Diesel Engine Oils), which is incorporated herein by reference. The API guideline defines a base stock as a lubricant component that may be manufactured using a variety of different processes. Groups I, II and III base stocks are mineral oils, each with specific ranges of the amount of saturates, sulfur content and viscosity index. Group IV base stocks are polyalphaolefins (PAO). Group V base stocks include all other base stocks not included in Group I, II, III, or IV.

The saturates levels, sulfur levels and viscosity indices for Group I, II, III, IV and V base stocks are listed in Table 1 below.

TABLE 1

| Group | Saturates (As determined by ASTM D 2007) | Sulfur (As determined by ASTM D 2270) | Viscosity Index (As determined by ASTM D 4294, ASTM D 4297 or ASTM D 3120) |
|---|---|---|---|
| I | Less than 90% saturates. | Greater than or equal to 0.03% sulfur. | Greater than or equal to 80 and less than 120. |
| II | Greater than or equal to 90% saturates. | Less than or equal to 0.03% sulfur. | Greater than or equal to 80 and less than 120. |
| III | Greater than or equal to 90% saturates. | Less than or equal to 0.03% sulfur. | Greater than or equal to 120. |
| IV | Defined as polyalphaolefins (PAO) | | |
| V | All other base stocks not included in Groups I, II, III or IV | | |

In certain embodiments, the base oil is selected from the group consisting of natural oils of lubricating viscosity, synthetic oils of lubricating viscosity and mixtures thereof. In some embodiments, the base oil includes base stocks obtained by isomerization of synthetic wax and slack wax, as well as hydrocrackate base stocks produced by hydrocracking (rather than solvent extracting) the aromatic and polar components of the crude. In other embodiments, the base oil of lubricating viscosity includes natural oils, such as animal oils, vegetable oils, mineral oils (e.g., liquid petroleum oils and solvent treated or acid-treated mineral oils of the paraffinic, naphthenic or mixed paraffinic-naphthenic types), oils derived from coal or shale, and combinations thereof. Some non-limiting examples of animal oils include bone oil, lanolin, fish oil, lard oil, dolphin oil, seal oil, shark oil, tallow oil, and whale oil. Some non-limiting examples of vegetable oils include castor oil, olive oil, peanut oil, rapeseed oil, corn oil, sesame oil, cottonseed oil, soybean oil, sunflower oil, safflower oil, hemp oil, linseed oil, tung oil, oiticica oil, jojoba oil, and meadow foam oil. Such oils may be partially or fully hydrogenated.

In some embodiments, the synthetic oils of lubricating viscosity include hydrocarbon oils and halo-substituted hydrocarbon oils such as polymerized and inter-polymerized olefins, alkylbenzenes, polyphenyls, alkylated diphenyl ethers, alkylated diphenyl sulfides, as well as their derivatives, analogues and homologues thereof, and the like. In other embodiments, the synthetic oils include alkylene oxide polymers, interpolymers, copolymers and derivatives thereof wherein the terminal hydroxyl groups can be modified by esterification, etherification, and the like. In further embodiments, the synthetic oils include the esters of dicarboxylic acids with a variety of alcohols. In certain embodiments, the synthetic oils include esters made from $C_5$ to $C_{12}$ monocarboxylic acids and polyols and polyol ethers. In further embodiments, the synthetic oils include tri-alkyl phosphate ester oils, such as tri-n-butyl phosphate and tri-iso-butyl phosphate.

In some embodiments, the synthetic oils of lubricating viscosity include silicon-based oils (such as the polyakyl-, polyaryl-, polyalkoxy-, polyaryloxy-siloxane oils and silicate oils). In other embodiments, the synthetic oils include liquid esters of phosphorus-containing acids, polymeric tetrahydrofurans, polyalphaolefins, and the like.

Base oil derived from the hydroisomerization of wax may also be used, either alone or in combination with the aforesaid natural and/or synthetic base oil. Such wax isomerate oil is produced by the hydroisomerization of natural or synthetic waxes or mixtures thereof over a hydroisomerization catalyst.

In further embodiments, the base oil comprises a poly-alpha-olefin (PAO). In general, the poly-alpha-olefins may be derived from an alpha-olefin having from about 2 to about 30, from about 4 to about 20, or from about 6 to about 16 carbon atoms. Non-limiting examples of suitable poly-alpha-olefins include those derived from octene, decene, mixtures thereof, and the like. These poly-alpha-olefins may have a viscosity from about 2 to about 15, from about 3 to about 12, or from about 4 to about 8 centistokes at 100° C. In some instances, the poly-alpha-olefins may be used together with other base oils such as mineral oils.

In further embodiments, the base oil comprises a polyalkylene glycol or a polyalkylene glycol derivative, where the terminal hydroxyl groups of the polyalkylene glycol may be modified by esterification, etherification, acetylation and the like. Non-limiting examples of suitable polyalkylene glycols include polyethylene glycol, polypropylene glycol, polyisopropylene glycol, and combinations thereof. Non-limiting examples of suitable polyalkylene glycol derivatives include ethers of polyalkylene glycols (e.g., methyl ether of polyisopropylene glycol, diphenyl ether of polyethylene glycol, diethyl ether of polypropylene glycol, etc.), mono- and polycarboxylic esters of polyalkylene glycols, and combinations thereof. In some instances, the polyalkylene glycol or polyalkylene glycol derivative may be used together with other base oils such as poly-alpha-olefins and mineral oils.

In further embodiments, the base oil comprises any of the esters of dicarboxylic acids (e.g., phthalic acid, succinic acid, alkyl succinic acids, alkenyl succinic acids, maleic acid, azelaic acid, suberic acid, sebacic acid, fumaric acid, adipic acid, linoleic acid dimer, malonic acid, alkyl malonic acids, alkenyl malonic acids, and the like) with a variety of alcohols (e.g., butyl alcohol, hexyl alcohol, dodecyl alcohol, 2-ethylhexyl alcohol, ethylene glycol, diethylene glycol monoether, propylene glycol, and the like). Non-limiting examples of these esters include dibutyl adipate, di(2-ethylhexyl) sebacate, di-n-hexyl fumarate, dioctyl sebacate, diisooctyl azelate, diisodecyl azelate, dioctyl phthalate, didecyl phthalate, dieicosyl sebacate, the 2-ethylhexyl diester of linoleic acid dimer, and the like.

In further embodiments, the base oil comprises a hydrocarbon prepared by the Fischer-Tropsch process. The Fischer-Tropsch process prepares hydrocarbons from gases containing hydrogen and carbon monoxide using a Fischer-Tropsch catalyst. These hydrocarbons may require further processing in order to be useful as base oils. For example, the hydrocarbons may be dewaxed, hydroisomerized, and/or hydrocracked using processes known to a person of ordinary skill in the art.

In further embodiments, the base oil comprises an unrefined oil, a refined oil, a rerefined oil, or a mixture thereof. Unrefined oils are those obtained directly from a natural or synthetic source without further purification treatment. Non-limiting examples of unrefined oils include shale oils obtained directly from retorting operations, petroleum oils obtained directly from primary distillation, and ester oils obtained directly from an esterification process and used without further treatment. Refined oils are similar to the unrefined oils except the former have been further treated by one or more purification processes to improve one or more properties. Many such purification processes are known to those skilled in the art such as solvent extraction, secondary distillation, acid or base extraction, filtration, percolation, and the like. Rerefined oils are obtained by applying to refined oils processes similar to those used to obtain refined oils. Such rerefined oils are also known as reclaimed or reprocessed oils and often are additionally treated by processes directed to removal of spent additives and oil breakdown products.

In certain embodiments, the compounds and compositions provided herein have use as pour point depressant additives. In another embodiment, provided herein are pour point depressant additive compositions comprising a compound of formula I-A, I-B, I-C, I-D, II-A, II-B, II-C, II-D or a combination thereof and a compatible solvent.

In certain embodiments, the compounds and compositions provided herein are used in combination with one or more other additives known in the art, for example the following: detergents, particulate emission reducers, storage stabilizers, antioxidants, corrosion inhibitors, dehazers, demulsifiers, antifoaming agents, cetane improvers, cosolvents, package compatibilizers, and lubricity additives.

In certain embodiments, the pour point depressant additive composition comprises between 0.1 and 75%, between 1 and 65%, or between 5 and 50% of the compound of formula I-A, I-B, I-C, I-D, II-A, II-B, II-C, II-D or a combination thereof in an oil or a solvent miscible with oil. Examples of solvent are organic solvents including hydrocarbon solvents, for example petroleum fractions such as naphtha, kerosene, diesel and heater oil; aromatic hydrocarbons; alcohols and/or esters; and paraffinic hydrocarbons such as hexane and pentane and isoparaffins. The solvent is selected based on its compatibility with the additive and with the oil. Examples of oils for use herein include, crude oil or fuel oil. In certain embodiments, the oil is a lubricating oil, which may be an animal, vegetable or mineral oil, such as petroleum oil fractions ranging from naphthas or spindle oil to SAE 30, 40 or 50 lubricating oil grades, castor oil, fish oils, oxidized mineral oil, or biodiesels. The pour point depressant compositions provided herein are useful in lubricating oils as flow improvers, pour point depressants or dewaxing aids.

In certain embodiments, the compounds and compositions provided herein have use as fuel additives in fuels used to, for example, power internal combustion engines such as reciprocating engines (e.g., gasoline engines and diesel engines), Wankel engines, jet engines, some rocket engines, missile engines, and gas turbine engines. The compounds and compositions provided herein can be used in combination with other fuel additives known in the art. Types of fuel additives include, but are not limited to, antioxidants, thermal stability improvers, cetane improvers, stabilizers, cold flow improvers, combustion improvers, anti-foams, anti-haze additives, corrosion inhibitors, lubricity improvers, icing inhibitors, injector cleanliness additives, smoke suppressants, drag reducing additives, metal deactivators, dispersants, detergents, demulsifiers, dyes, markers, static dissipaters, biocides, and combinations thereof.

Methods of Preparation

The farnesene dimers and/or farnesane dimers for use in compositions provided herein can be prepared dimerization of β-farnesene as described in Example 1. In some embodiments, β-farnesene is derived from an isoprenoid starting material. In certain embodiments, the isoprenoid starting material is made by host cells by converting a carbon source into the isoprenoid starting material. Exemplary methods for making β-farnesene are described in U.S. Pat. No. 7,399,323 which is incorporated by reference in its entirety.

The hydrogenated dimers of formula II-A, II-B, II-C and II-D can be prepared by reducing the dimers of formula I-A, I-B, I-C and I-D in the presence of hydrogen with a catalyst such as Pd, Pd/C, Pt, $PtO_2$, $Ru(PPh_3)_2Cl_2$, Raney nickel, or combinations thereof.

In one embodiment, the catalyst is a Pd catalyst. In another embodiment, the catalyst is 5% Pd/C or 10% Pd/C. Alternatively, any reducing agent that can reduce a C=C bond to a C—C bond can also be used. For example, hydrazine in the presence of a catalyst, such as 5-ethyl-3-methyllumiflavinium perchlorate, under $O_2$ atmosphere can be used to give the corresponding hydrogenated products. The reduction reaction with hydrazine is disclosed in Imada et al., *J. Am. Chem. Soc.*, 127, 14544-14545 (2005), which is incorporated herein by reference.

The compositions disclosed herein can be prepared by any method known to a person of ordinary skill in the art for making lubricating oils. In some embodiments, one or more farnesene dimers in the lubricating oil compositions are blended or mixed with other components, such as one or more lubricating oil additives. Exemplary lubricating oil additives are described below. Any mixing or dispersing equipment known to a person of ordinary skill in the art may be used for blending, mixing or solubilizing the ingredients.

The following additive components are examples of some of the components that can be added to compositions provided herein. These examples of additives are provided to illustrate the compositions, but they are not intended to limit them.

Additives

Optionally, the composition may further comprise at least one additive or a modifier (hereinafter designated as "additive") that can impart or improve any desirable property of the composition. In certain embodiments, the additive is a lubricating oil additive. Any lubricating oil additive known to a person of ordinary skill in the art may be used in the compositions disclosed herein. Some suitable additives have been described in Mortier et al., "*Chemistry and Technology of Lubricants,*" 2nd Edition, London, Springer, (1996); and Leslie R. Rudnick, "*Lubricant Additives: Chemistry and Applications,*" New York, Marcel Dekker (2003), both of which are incorporated herein by reference. In some embodiments, the additive can be selected from the group consisting of antioxidants, antiwear agents, detergents, rust inhibitors, demulsifiers, friction modifiers, multi-functional additives, pour point depressants, foam inhibitors, metal deactivators, dispersants, corrosion inhibitors, thermal stability improvers, dyes, markers, and combinations thereof.

In general, the concentration of each of the additives in the composition, when used, may range from about 0.001 wt. % to about 20 wt. %, from about 0.01 wt. % to about 10 wt. %, from about 0.1 wt. % to about 5 wt. % or from about 0.1 wt. % to about 2.5 wt. %, based on the total weight of the composition. Further, the total amount of the additives in the composition may range from about 0.001 wt. % to about 30 wt. %, from about 0.01 wt. % to about 20 wt. %, from about 0.1 wt. % to about 10 wt. %, or from about 0.1 wt. % to about 5 wt. %, based on the total weight of the composition.

Metal Detergents

In some embodiments, a composition provided herein comprises at least a neutral or overbased metal detergent as an additive, or additive components. In certain embodiments, the metal detergent prevents the formation of deposits on the surface of an engine. In certain embodiments, the detergent have additional functions, for example, as antioxidant. In certain aspects, compositions contain metal detergents comprising either overbased detergents or mixtures of neutral and overbased detergents. The term "overbased" is intended to define additives which contain a metal content in excess of that required by the stoichiometry of the particular metal and the particular organic acid used. The excess metal exists in the form of particles of inorganic base, e.g. a hydroxide or carbonate, surrounded by a sheath of metal salt. The sheath serves to maintain the particles in dispersion in a liquid oleaginous vehicle. The amount of excess metal is commonly expressed as the ratio of total equivalence of excess metal to equivalence of organic acid and is typically 0.1 to 30.

Some non-limiting examples of suitable metal detergents include sulfurized or unsulfurized alkyl or alkenyl phenates, alkyl or alkenyl aromatic sulfonates, borated sulfonates, sulfurized or unsulfurized metal salts of multi-hydroxy alkyl or alkenyl aromatic compounds, alkyl or alkenyl hydroxy aromatic sulfonates, sulfurized or unsulfurized alkyl or alkenyl naphthenates, metal salts of alkanoic acids, metal salts of an alkyl or alkenyl multiacid, and chemical and physical mixtures thereof. Other non-limiting examples of suitable metal detergents include metal sulfonates, phenates, salicylates, phosphonates, thiophosphonates and combinations thereof. The metal can be any metal suitable for making sulfonate, phenate, salicylate or phosphonate detergents. Non-limiting examples of suitable metals include alkali metals, alkaline metals and transition metals. In some embodiments, the metal is Ca, Mg, Ba, K, Na, Li or the like. An exemplary metal detergent which may be employed in the compositions includes overbased calcium phenate.

Generally, the amount of the metal detergent additive can be less than 10000 ppm, less than 1000 ppm, less than 100 ppm, or less than 10 ppm, based on the total weight of the composition. In some embodiments, the amount of the metal detergent is from about 0.001 wt. % to about 5 wt. %, from about 0.05 wt. % to about 3 wt. %, or from about 0.1 wt. % to about 1 wt. %, based on the total weight of the composition. Some suitable detergents have been described in Mortier et al., "*Chemistry and Technology of Lubricants,*" 2nd Edition, London, Springer, Chapter 3, pages 75-85 (1996); and Leslie R. Rudnick, "*Lubricant Additives: Chemistry and Applications,*" New York, Marcel Dekker, Chapter 4, pages 113-136 (2003), both of which are incorporated herein by reference.

Solubilizing Agents

Solubilizing agents may be used in compositions provided herein to increase solubility of various components in the composition. Suitable solubilizing agents include, but are not limited to, oil-soluble esters and diesters, alkylated naphthalenes, alkylated sulfones, naphthenic type base oils, aromatic type base oils, and alkylated benzenes. Other solubilizing agents known in the art are also contemplated herein. The esters and diesters that may be used as solublizing agents include, for example, adipate esters and polyol esters. Exemplary diesters include the adipates, azelates, and sebacates of $C_8$-$C_{13}$ alkanols (or mixtures thereof), the phthalates of $C_4$-$C_{13}$ alkanols (or mixtures thereof). Mixtures of two or more different types of diesters (e.g., dialkyl adipates and dialkyl azelates, etc.) may also be used. Examples of such materials include the n-octyl, 2-ethylhexyl, isodecyl, and tridecyl diesters of adipic acid, azelaic acid, and sebacic acid, and the n-butyl, isobutyl, pentyl, hexyl, heptyl, octyl, nonyl, decyl, undecyl, dodecyl, and tridecyl diesters of phthalic acid.

Anti Wear and/or Extreme Pressure Agents

In certain embodiments, compositions disclosed herein can additionally comprise anti wear or extreme pressure agents. Wear occurs in all equipment that has moving parts in contact. Specifically, three conditions commonly lead to wear in engines: (1) surface-to-surface contact; (2) surface contact with foreign matter; and (3) erosion due to corrosive materials. Wear resulting from surface-to-surface contact is friction or adhesive wear, from contact with foreign matter is abrasive wear, and from contact with corrosive materials is corrosive wear. Fatigue wear is an additional type of wear that is common in equipment where surfaces are not only in contact but also experience repeated stresses for prolonged periods. Abrasive wear can be prevented by installing an efficient filtration mechanism to remove the offending debris. Corrosive wear can be addressed by using additives which neutralize the reactive species that would otherwise attack the metal surfaces. The control of adhesive wear requires the use of additives called antiwear and extreme-pressure (EP) agents.

Under optimal conditions of speed and load, the metal surfaces of the equipment should be effectively separated by a lubricant film. Increasing load, decreasing speed, or otherwise deviating from such optimal conditions promote metal-to-metal contact. This contact typically causes a temperature increase in the contact zone due to frictional heat, which in turn leads to the loss of lubricant viscosity and hence its film-forming ability. In certain embodiments, antiwear additive and EP agents offer protection by a similar mechanism. In certain embodiments, EP additives require higher activation temperatures and load than antiwear additives.

Without being bound to any particular theory, it is believed that antiwear and/or EP additives function by thermal decomposition and by forming products that react with the metal surface to form a solid protective layer. This solid metal film fills the surface asperities and facilitates effective film formation, thereby reducing friction and preventing welding and surface wear.

Most antiwear and extreme pressure agents contain sulfur, chlorine, phosphorus, boron, or combinations thereof. The classes of compounds that inhibit adhesive wear include, for example, alkyl and aryl disulfides and polysulfides; dithiocarbamates; chlorinated hydrocarbons; and phosphorus compounds such as alkyl phosphites, phosphates, dithiophosphates, and alkenylphosphonates.

Exemplary antiwear agents that can be included in compositions provided herein include metal (e.g., Pb, Sb, and the like) salts of dithiophosphate, metal (e.g., Pb, Sb, and the like) salts of dithiocarbamate, metal (e.g., Pb, Sb and the like) salts of fatty acids, boron compounds, phosphate esters, phosphite esters, amine salts of phosphoric acid esters or thiophosphoric acid esters, reaction products of dicyclopentadiene and thiophosphoric acids and combinations thereof. The amount of the anti-wear agent may vary from about 0.01 wt. % to about 5 wt. %, from about 0.05 wt. % to about 3 wt. %, or from about 0.1 wt. % to about 1 wt. %, based on the total weight of the composition. Some suitable anti-wear agents have been described in Leslie R. Rudnick, "*Lubricant Additives: Chemistry and Applications*," New York, Marcel Dekker, Chapter 8, pages 223-258 (2003), which is incorporated herein by reference.

In one embodiment, the sulfated ash content of the total composition is less than 5 wt. %, less than 4 wt. %, less than 3 wt. %, less than 2 wt. %, or less than 1 wt. %, as measured according to ASTM D874.

In one embodiment, the EP agents for use in compositions provided herein include alkyl and aryl disulfides and polysulfides, dithiocarbamates, chlorinated hydrocarbons, dialkyl hydrogen phosphites, and salts of alkyl phosphoric acids. Methods of making these EP agents are known in the art. For example, polysulfides are synthesized from olefins either by reacting with sulfur or sulfur halides, followed by dehydrohalogenation. Dialkydithiocarbamates are prepared either by neutralizing dithiocarbamic acid (which can be prepared by reacting a diakylamine and carbon disulfide at low temperature) with bases, such as antimony oxide, or by its addition to activated olefins, such as alkyl acrylates.

In certain embodiments, compositions provided herein comprise one or more EP agents. In one embodiment, use of more that one EP agent leads to synergism. For example, synergism may be observed between sulfur and chlorine-containing EP agents. An exemplary composition provided herein includes one or more EP agents selected from: zinc dialkyldithiophosphate (primary alkyl type & secondary alkyl type), sulfurized oils, diphenyl sulfide, methyl trichlorostearate, chlorinated naphthalene, fluoroalkylpolysiloxane, and lead naphthenate.

Rust Inhibitors (Anti Rust Agents)

Protection against rust is an important consideration in formulating lubricants. Without protection, rust ultimately causes a loss of metal, thereby lowering the integrity of the equipment, and resulting in engine malfunction. In addition, corrosion exposes fresh metal that can wear at an accelerated rate, perpetuated by the metal ions that might be released into the fluid and act as oxidation promoters.

The composition disclosed herein can optionally comprise a rust inhibitor that can inhibit the corrosion of metal surfaces. Any rust inhibitor known by a person of ordinary skill in the art may be used in the composition. The rust inhibitors attach themselves to metal surfaces to form an impenetrable protective film, which can be physically or chemically adsorbed to the surface. Specifically, film formation occurs when the additives interact with the metal surface via their polar ends and associate with the lubricant via their nonpolar ends. Suitable rust inhibitors may include, for example, various nonionic polyoxyethylene surface active agents such as polyoxyethylene lauryl ether, polyoxyethylene higher alcohol ether, polyoxyethylene nonylphenyl ether, polyoxyethylene octylphenyl ether, polyoxyethylene octyl stearyl ether, polyoxyethylene oleyl ether, polyoxyethylene sorbitol monostearate, polyoxyethylene sorbitol mono-oleate, and polyethylene glycol monooleate. Suitable rust inhibitors may further include other compounds such as, for example, monocarboxylic acids (e.g., 2-ethylhexanoic acid, lauric acid, myristic acid, palmitic acid, oleic acid, linoleic acid, linolenic acid, behenic acid, cerotic acid and the like), oil-soluble polycarboxylic acids (e.g., those produced from tall oil fatty acids, oleic acid, linoleic acid and the like), alkenylsuccinic acids in which the alkenyl group contains 10 or more carbon atoms (e.g., tetrapropenylsuccinic acid, tetradecenylsuccinic acid, hexadecenylsuccinic acid, and the like); long-chain alpha, omega-dicarboxylic acids having a molecular weight in the range of 600 to 3000 daltons and combinations thereof. Further examples of rust agents include metal soaps, fatty acid amine salts, metal salts of heavy sulfonic acid, partial carboxylic acid ester of polyhydric alcohol, and phosphoric ester.

Demulsifiers

The composition disclosed herein can optionally comprise a demulsifier that can promote oil-water separation in compositions that are exposed to water or steam. Any demulsifier known by a person of ordinary skill in the art may be used in the composition. Non-limiting examples of suitable demulsifiers include anionic surfactants (e.g., alkyl-naphthalene sulfonates, alkyl benzene sulfonates and the like), nonionic alkoxylated alkylphenol resins, polymers of alkylene oxides (e.g., polyethylene oxide, polypropylene oxide, block copolymers of ethylene oxide, propylene oxide and the like), esters of oil soluble acids, polyoxyethylene sorbitan ester and combinations thereof. In certain embodiments, the demulsifiers for use herein include block copolymers of propylene oxide or ethylene oxide and initiators, such as, for example, glycerol, phenol, formaldehyde resins, soloxanes, polyamines, and polyols. In certain embodiments, the polymers contain about 20 to about 50% ethylene oxide. These materials concentrate at the water-oil interface and create low viscosity zones, thereby promoting droplet coalescence and gravity-driven phase separation. Low molecular weight materials, such as, for example, alkali metal or alkaline earth metal salts of dialkylnaphthalene sulfonic acids, are also useful in certain applications. The amount of the demulsifier may vary from about 0.01 wt. % to about 10 wt. %, from about 0.05 wt. % to about 5 wt. %, or from about 0.1 wt. % to about 3 wt. %, based on the total weight of the composition. Some suitable demulsifiers have been described in Mortier et al., "*Chemistry and Technology of Lubricants,*" 2nd Edition, London, Springer, Chapter 6, pages 190-193 (1996), which is incorporated herein by reference.

Friction Modifiers

The composition disclosed herein can optionally comprise a friction modifier that can lower the friction between moving parts. Any friction modifier known by a person of ordinary skill in the art may be used in the composition. They are typically long-chain molecules with a polar end group and a nonpolar linear hydrocarbon chain. The polar end groups either physically adsorb onto the metal surface or chemically react with it, while the hydrocarbon chain extends into the lubricant. The chains associated with one another and the lubricant to form a strong lubricant film.

Non-limiting examples of suitable friction modifiers include fatty carboxylic acids; derivatives (e.g., alcohol, esters, borated esters, amides, metal salts and the like) of fatty carboxylic acid; mono-, di- or tri-alkyl substituted phosphoric acids or phosphonic acids; derivatives (e.g., esters, amides, metal salts and the like) of mono-, di- or tri-alkyl substituted phosphoric acids or phosphonic acids; mono-, di- or tri-alkyl substituted amines; mono- or di-alkyl substituted amides and combinations thereof.

In one embodiment, the friction modifier is a saturated fatty acid containing a 13 to 18 carbon chains. The amount of the friction modifier may vary from about 0.01 wt. % to about 10 wt. %, from about 0.05 wt. % to about 5 wt. %, or from about 0.1 wt. % to about 3 wt. %, based on the total weight of the composition. Some suitable friction modifiers have been described in Mortier et al., "*Chemistry and Technology of Lubricants,*" 2nd Edition, London, Springer, Chapter 6, pages 183-187 (1996); and Leslie R. Rudnick, "*Lubricant Additives: Chemistry and Applications,*" New York, Marcel Dekker, Chapters 6 and 7, pages 171-222 (2003), both of which are incorporated herein by reference.

Seal Swell Agents

Seal swell agents may be included in the finished compositions of the disclosed embodiments particularly when compositions provided herein are used as power transmission fluids. Suitable seal swell agents may be selected from oil-soluble diesters, oil-soluble sulfones, silicon containing organic compounds, and mixtures thereof. Generally speaking the most suitable diesters include the adipates, azelates, and sebacates of $C_8$-$C_{13}$ alkanols (or mixtures thereof), and the phthalates of $C_4$-$C_{13}$ alkanols (or mixtures thereof). Mixtures of two or more different types of diesters (e.g., dialkyl adipates and dialkyl azelates, etc.) may also be used. Examples of such materials include the n-octyl, 2-ethylhexyl, isodecyl, and tridecyl diesters of adipic acid, azelaic acid, and sebacic acid, and the n-butyl, isobutyl, pentyl, hexyl, heptyl, octyl, nonyl, decyl, undecyl, dodecyl, and tridecyl diesters of phthalic acid. Other esters which may give generally equivalent performance are polyol esters.

In one embodiment, the seal swell agents are the oil-soluble dialkyl esters of (i) adipic acid, (ii) sebacic acid, or (iii) phthalic acid.

Pour Point Depressants

The composition disclosed herein can optionally comprise a pour point depressant that can lower the pour point of the composition. Any pour point depressant known by a person of ordinary skill in the art may be used in the composition. In certain embodiments, pour point depressants possess one or more structural features selected from: (1) polymeric structure; (2) waxy and non-waxy components; (3) comb structure comprising a short backbone with long pendant groups; and (4) broad molecular weight distribution. Non-limiting examples of suitable pour point depressants include polymethacrylates, alkyl acrylate polymers, alkyl methacrylate polymers, alkyl fumarate polymers, di(tetra-paraffin phenol) phthalate, condensates of tetra-paraffin phenol, condensates of a chlorinated paraffin with naphthalene, alkylated naphthalenes, styrene esters, oligomerized alkyl phenols, phthalic acid esters, ethylene-vinyl acetate copolymers and combinations thereof. In one embodiment, the pour point depressant is selected from tetra (long-chain) alkyl silicates, phenyltristearyloxysilane, and pentaerythritol tetrastearate. In some embodiments, the pour point depressant comprises an ethylene-vinyl acetate copolymer, a condensate of chlorinated paraffin and phenol, polyalkyl styrene or the like. The amount of the pour point depressant may vary from about 0.01 wt. % to about 10 wt. %, from about 0.05 wt. % to about 5 wt. %, or from about 0.1 wt. % to about 3 wt. %, based on the total weight of the composition. Some suitable pour point depressants have been described in Mortier et al., "*Chemistry and Technology of Lubricants,*" 2nd Edition, London, Springer, Chapter 6, pages 187-189 (1996); and Leslie R. Rudnick, "*Lubricant Additives. Chemistry and Applications,*" New York, Marcel Dekker, Chapter 11, pages 329-354 (2003), both of which are incorporated herein by reference.

Foam Inhibitors

The composition disclosed herein can optionally comprise a foam inhibitor or an anti-foam that can break up foams in oils. Any foam inhibitor or anti-foam known by a person of ordinary skill in the art may be used in the composition. Non-limiting examples of suitable anti-foams include silicone oils or polydimethylsiloxanes, fluorosilicones, alkoxylated aliphatic acids, polyethers (e.g., polyethylene glycols), branched polyvinyl ethers, alkyl acrylate polymers, alkyl methacrylate polymers, polyalkoxyamines and combinations thereof. In some embodiments, the anti-foam comprises glycerol monostearate, polyglycol palmitate, a trialkyl monothiophosphate, an ester of sulfonated ricinoleic acid, benzoylacetone, methyl salicylate, glycerol monooleate, or glycerol dioleate. The amount of the anti-foam may vary from about 0.01 wt. % to about 5 wt. %, from about 0.05 wt. % to about 3 wt. %, or from about 0.1 wt. % to about 1 wt. %, based on the total weight of the composition. Some suitable anti-foams have been described in Mortier et al., "*Chemistry and Technology of Lubricants,*" 2nd Edition, London, Springer, Chapter 6, pages 190-193 (1996), which is incorporated herein by reference.

Metal Deactivators

In some embodiments, the composition comprises at least a metal deactivator. Some non-limiting examples of suitable metal deactivators include disalicylidene propylenediamine, triazole derivatives, thiadiazole derivatives, and mercaptobenzimidazoles.

Dispersants

The composition disclosed herein can optionally comprise a dispersant that can prevent sludge, varnish, and other deposits by keeping particles suspended in a colloidal state. In certain embodiments, dispersants perform these functions via one or more means selected from: (1) solubilizing polar contaminants in their micelles; (2) stabilizing colloidal dispersions in order to prevent aggregation of their particles and their separation out of oil; (3) suspending such products, if they form, in the bulk lubricant; (4) modifying soot to minimize its aggregation and oil thickening; and (5) lowering surface/interfacial energy of undesirable materials to decrease their tendency to adhere to surfaces. The undesirable materials are typically formed as a result of oxidative degradation of the lubricant, the reaction of chemically reactive species such as carboxylic acids with the metal surfaces in the engine, or the decomposition of thermally unstable lubricant additives such as, for example, extreme pressure agents.

In certain aspects, a dispersant molecule comprises three distinct structural features: (1) a hydrocarbyl group; (2) a polar group; and (3) a connecting group or a link. In certain embodiments, the hydrocarbyl group is polymeric in nature, and has a molecular weight of at or above about 2000 Daltons, in one embodiment, at or above about 3000 Daltons, in another embodiment, at or above about 5000 Daltons, and in yet another embodiment, at or above about 8000 Daltons. A variety of olefins, such as polyisobutylene, polypropylene, polyalphaolefins, and mixtures thereof, can be used to make suitable polymeric dispersants. In certain embodiments, the polymeric dispersant is a polyisobutylene-derived dispersant. Typically the number average molecular weight of polyisobutylene in those dispersants ranges between about 500 and about 3000 Daltons, or, in some embodiments, between about 800 to about 2000 Daltons, or in further embodiments, between about 1000 to about 2000 Daltons. In certain embodiments, the polar group in the dispersant is nitrogen- or oxygen-derived. Nitrogen-based dispersants are typically derived from amines. The amines from which the nitrogen-based dispersants are derived are often polyalkylenepolyamines, such as, for example, diethylenetriamine and trethylenetetramine. Amine-derived dispersants are also called nitrogen- or amine-dispersants, while those derived from alcohol are also called oxygen or ester dispersants. Oxygen-based dispersants are typically neutral while the amine-based dispersants are typically basic.

Non-limiting examples of suitable dispersants include alkenyl succinimides, alkenyl succinimides modified with other organic compounds, alkenyl succinimides modified by post-treatment with ethylene carbonate or boric acid, succinamides, succinate esters, succinate ester-amides, pentaerythritols, phenate-salicylates and their post-treated analogs, alkali metal or mixed alkali metal, alkaline earth metal borates, dispersions of hydrated alkali metal borates, dispersions of alkaline-earth metal borates, polyamide ashless dispersants, benzylamines, Mannich type dispersants, phosphorus-containing dispersants, and combinations thereof. The amount of the dispersant may vary from about 0.01 wt. % to about 10 wt. %, from about 0.05 wt. % to about 7 wt. %, or from about 0.1 wt. % to about 4 wt. %, based on the total weight of the composition. Some suitable dispersants have been described in Mortier et al., "*Chemistry and Technology of Lubricants,*" 2nd Edition, London, Springer, Chapter 3, pages 86-90 (1996); and Leslie R. Rudnick, "*Lubricant Additives: Chemistry and Applications,*" New York, Marcel Dekker, Chapter 5, pages 137-170 (2003), both of which are incorporated herein by reference.

Anti-Oxidants

Optionally, the composition disclosed herein can further comprise an additional antioxidant that can reduce or prevent the oxidation of the base oil. Any antioxidant known by a person of ordinary skill in the art may be used in the composition. Examples of anti oxidants useful in compositions provided herein include, but are not limited to, phenol type (phenolic) oxidation inhibitors, such as 4,4' methylene bis (2,6 di tert butylphenol), 4,4' bis(2,6 di tert-butylphenol), 4,4' bis (2 methyl 6 tert butylphenol), 2,2' methylene bis(4-methyl 6 tert butylphenol), 4,4' butylidene bis (3 methyl 6 tert butylphenol), 4,4' isopropylidene bis(2,6 di tert butylphenol), 2,2' methylene bis(4-methyl 6 nonylphenol), 2,2' isobutylidene bis(4,6 dimethylphenol), 2,2' 5 methylene bis (4 methyl 6 cyclohexylphenol), 2,6 di tert butyl 4-methylphenol, 2,6 di tert butyl 4 ethylphenol, 2,4 dimethyl 6 tert butyl-phenol, 2,6 di tert 1 dimethylamino p cresol, 2,6 di tert 4 (N,N'-dimethylaminomethylphenol), 4,4' thiobis (2 methyl 6 tert butylphenol), 2,2'-thiobis (4 methyl 6 tert butylphenol), bis (3 methyl 4 hydroxy 5 tert-10 butylbenzyl) sulfide, and bis(3,5 di tert butyl 4 hydroxybenzyl). Diphenylamine type oxidation inhibitors include, but are not limited to, alkylated diphenylamine, phenyl alpha naphthylamine, and alkylated alpha naphthylamine, sulfur-based antioxidants (e.g., dilauryl-3,3'-thiodipropionate, sulfurized phenolic antioxidants and the like), phosphorous-based antioxidants (e.g., phosphites and the like), zinc dithiophosphate, oil-soluble copper compounds and combinations thereof. Other types of oxidation inhibitors include metal dithiocarbamate (e.g., zinc dithiocarbamate), and 15 methylenebis(dibutyldithiocarbamate). The amount of the antioxidant may vary from about 0.01 wt. % to about 10 wt. %, from about 0.05 wt. % to about 5 wt. %, or from about 0.1 wt. % to about 3 wt. %, based on the total weight of the composition. Some suitable antioxidants have been described in Leslie R. Rudnick, "*Lubricant Additives: Chemistry and Applications,*" New York, Marcel Dekker, Chapter 1, pages 1-28 (2003), which is incorporated herein by reference.

Multifunctional Additives

Various additives mentioned or not mentioned herein can provide a multiplicity of effects to the lubricant oil composition provided herein. Thus, for example, a single additive may act as a dispersant as well as an oxidative inhibitor. Multifunctional additives are well known in the art. Other suitable multi-functional additives may include, for example, sulfurized oxymolybdenum dithiocarbamate, sulfurized oxymolybdenum organo pohosphoro dithioate, oxymolybdenum monoglyceride, amine-molybdenum complex compound, and sulfur-containing molybdenum complex compounds.

Viscosity Index Improvers

In certain embodiments, the composition comprises at least a viscosity index improver. Some non-limiting examples of suitable viscosity index improvers include polymethacrylate type polymers, ethylene-propylene copolymers, styrene-isoprene copolymers, hydrated styrene-isoprene copolymers, polyisobutylene, and dispersant type viscosity index improvers.

Conductivity Enhancers

In certain embodiments, the composition comprises at least a conductivity enhancer. Some non-limiting examples of suitable conductivity enhancers include hydrogenated lecithin and related compounds; magnesium palmitate or aluminum palmitate or stearate; dihexyl esters of phosphoric acid neutralized with tetramethylnonylamines or C11-C14-alkylamines; monosodium phosphate derivatives of mono- and diglycerides composed of glyceride derivatives formed by reacting mono- and diglycerides that are derived from edible sources with phosphorus pentoxide (tetraphosphorus decoxide) followed by neutralization with sodium carbonate; phosphate derivatives of mono- and diglycerides produced as described above and reacted with ethanolamine and neutralized with fatty acid, and sodium dodecyl sulfonate.

Load-Bearing Additives

In certain embodiments, the composition comprises one or more load-bearing additives to reduce friction during metal work processing. Exemplary load-bearing additives include, but are not limited to fatty alcohols, dicarboxylic acids or fatty acids and esters thereof, for instance fatty acid esters, butyl stearate, butyl palmitate, tridecyl azelate and/or dioctyl sebacate.

Uses of the Compositions

The compositions provided herein are used in a wide variety of industrial applications associated with the automotive, tractor, airline, and railroad industries for use in engine oils, transmission fluids, hydraulic fluids, gear oils, energy/shock absorbers power steering; metal-working industry for use in metal sheets rolling or cutting machines and water coolants; process oils for use in rubber and plastic processing; marine oils for use in propel engines; quench fluids; greases; crankcase lubricants; vehicle axle applications; and rotating machinery such as stationary engines, pumps, gas turbines, compressors, wind turbines, and the like. Stationary engines include fuel and gas powered engines that are not associated with the automotive, tractor, airline, and railroad industries. Exemplary automotive applications include, but are not limited to use in engine oils, for example, internal combustion engines, natural gas engines, turbine engines, automatic and manual transmissions and marine diesel engines. In certain embodiments, compositions provided herein have use as industrial oils, such as in hydraulic oils, fire-resistant oils, industrial gear oils, railroad diesel and natural gas. In addition, the products based on embodiments described herein may be used in planetary hub reduction axles, mechanical steering and transfer gear boxes in utility vehicles such as trucks, synchromesh gear boxes, as well as power take-off gears, limited slip axles, and planetary hub reduction gear boxes.

In one embodiment, compositions provided herein are useful as engine lubricants. In one embodiment, provided herein is a method of lubricating an engine comprising operating the engine in contact with a composition provided herein.

In certain embodiments, provided herein is a method of lubricating a machine by operating the machine in contact with a composition provided herein. The compositions can be used for lubricating any machine that needs lubrication. Exemplary machines include, but are not limited to engines, pumps, gas turbines, compressors, wind turbines, and the like. In certain embodiments, the engine is a fuel and/or gas powered engine associated with the automotive, tractor, airline, and railroad industries. In certain embodiments, the engine is a stationary engine, including a fuel and/or gas powered engine that is not associated with the automotive, tractor, airline, and railroad industries. In certain embodiments, provided herein is a machine comprising a composition provided herein.

In one embodiment, a composition provided herein is an automatic transmission fluid (ATF). An exemplary ATF composition contains one or more farnesene dimers and/or farnesane dimers provided herein, a solubilizing agent, from about 0.5 to about 1.5 wt. % viscosity index improver, from about 1.5 to about 2.5 wt. % ashless dispersant, from about 0.05 to about 1 wt. % friction modifier, from about 0.01 to about 0.5 wt. % corrosion inhibitor, from about 0.1 to about 0.4 wt. % antiwear additive, from about 0.005 to about 5 wt. % metal deactivator, from about 0.1 to about 15 wt. % metallic detergent, from about 0.25 to about 1 wt. % seal swell agent, from about 0.01 to about 0.5 wt. % pour point depressant and optionally a base oil component.

In one embodiment, the finished composition is a manual transmission oil. An exemplary manual transmission lubricating oil formulation contains one or more farnesene dimers and/or farnesane dimers provided herein, a solubilizing agent, a viscosity index improver, an ashless dispersant, at least one antioxidant, at least one inhibitor and optionally a base oil component.

In another embodiment of the disclosure, the finished composition is an axle lubricating oil. An exemplary axle lubricating oil formulation contains a solubilizing agent, a viscosity index improver, a sulfur containing extreme pressure agent, at least one phosphorus containing anti-wear agent, at least one ashless dispersant, at least one inhibitor and optionally a base oil component.

In one embodiment, compositions provided herein are used as a crankcase lubricant and may include a solubilizing agent, a viscosity index improver, a detergent, a dispersant, an anti-wear agent, a friction modifier, an antioxidant, a corrosion inhibitor, a pour point depressant, an anti-foam agent and optionally a base oil component.

The compositions described herein may also be used in quench fluid applications to provide a slower rate of cooling for hardening metals such as steel. Quench fluid performance may be modified by introducing one or more of the foregoing additives and/or compositions to improve wettability, cooling rates, oil stability life, and to reduce deposit forming tendencies of the quench fluids.

While the compounds, compositions and methods have been described with respect to a limited number of embodiments, the specific features of one embodiment should not be attributed to other embodiments described herein. No single embodiment is representative of all aspects of the compositions or methods. In some embodiments, the compositions or methods may include numerous compounds or steps not mentioned herein. In other embodiments, the compositions or methods do not include, or are substantially free of, any compounds or steps not enumerated herein. Variations and modifications from the described embodiments exist.

All publications and patent applications mentioned in this specification are herein incorporated by reference to the same extent as if each individual publication or patent application was specifically and individually indicated to be incorporated by reference. Although the foregoing has been described in some detail by way of illustration and example for purposes of clarity of understanding, it will be readily apparent to those of ordinary skill in the art in light of the teachings herein that certain changes and modifications may be made thereto without departing from the spirit or scope of the appended claims.

EXAMPLES

The practice of the present subject matter can employ, unless otherwise indicated, conventional techniques in the industry and the like, which are within the skill of the art. To the extent such techniques are not described fully herein, one can find ample reference to them in the scientific literature.

In the following examples, efforts have been made to ensure accuracy with respect to numbers used (for example, amounts, temperature, and so on), but variation and deviation can be accommodated, and in the event a clerical error in the numbers reported herein exists, one of ordinary skill in the arts can deduce the correct amount in view of the remaining disclosure herein. Unless indicated otherwise, temperature is reported in degrees Celsius. All reagents, unless otherwise indicated, were obtained commercially. β-farnesene used herein is prepared as described in U.S. Pat. No. 7,399,323 which is incorporated by reference in its entirety. The following examples are intended for illustrative purposes only and do not limit in any way the scope of the present invention.

Example 1

This example describes a method for making farnesene dimers from β-farnesene.

To a 500 mL three-necked round-bottomed flask, previously rinsed with conc. NH$_4$OH solution and dried, equipped with a magnetic stirrer, heating mantle, thermometer, reflux condenser and nitrogen inlet were added 204 g (1.00 mol) of β-farnesene (Bedoukian, 98%). The farnesene was stirred and heated to 220° C. while monitoring the progress of the reaction by GC/MS. After two hours the colorless reaction mixture consisted almost entirely of two pairs of dimers, I-A:I-C in a ratio of 4:1 and I-B:I-D in a ratio of 4:1 with <2% of starting material remaining. The mixture was allowed to cool to approximately 50° C. and vacuum filtered through a 0.5 cm thick layer of Celite on a 60 mL medium porosity sintered glass funnel to afford 200 g (98.3%) of clear colorless oil. The compositions comprise compounds I-A, I-C, I-B, and I-D which was confirmed by $^1$H and $^{13}$C NMR.

Farnesene dimers: $^1$H (400 MHz, CDCl$_3$) d (multiplicity, coupling constant{s}, integration*), 5.71 (dd, J=5.6 and 10.8 Hz, 0.04H), 5.65 (dd, J=5.6 and 10.8 Hz, 0.04H), 5.37 (m, 0.60H), 5.12 (m, 3.04H), 5.01 (dt, J=1.6 and 10.8 Hz, 0.10H), 4.89 (ddd, J=1.6, 12.0 and 17.6 Hz, 0.06H), 4.74 (m, 1.00H), 2.09 (m, 9.28H), 1.98 (m, 5.30H), 1.68 (s, 4.24H), 1.60 (s, 7.97H) ppm.

Farnesene dimers: ¹³C (100 MHz, CDCl₃) δ 154.36, 154.26, 146.14, 145.44, 145.25, 139.55, 139.04, 137.46, 137.39, 136.94, 135.87, 135.38, 135.11, 135.07, 134.94, 134.82, 134.59, 131.225, 125.01, 124.97, 124.44, 124.34, 124.23, 124.06, 122.71, 120.47, 120.37, 120.17, 119.16, 115.71, 113.02, 112.11, 112.01, 107.24, 107.18, 40.39, 40.25, 40.17, 40.13, 40.00, 39.74, 38.72, 38.16, 38.04, 37.87, 37.61, 34.89, 34.63, 34.55, 32.27, 31.76, 31.47, 29.10, 28.41, 28.03, 27.25, 26.77, 26.65, 26.43, 26.41, 26.34, 25.88, 25.82, 25.69, 22.73, 22.46, 22.41, 17.68, 16.05, 16.02, 15.93 ppm.

* Integration values are relative areas peak to peak and not absolute numbers of protons.

Example 2

This example describes method for making farnesane dimers from farnesene dimers.

A mixture of farnesene dimers (100 g, 0.245 mol) was placed in a 1 L glass lined Hastaloy Parr hydrogenation vessel containing 0.75 g of 5% Pd/C. Hexane (300 mL) was added and the reactor assembled. The mixture was placed under vacuum for one hour. The stirrer was started (400 rpm) and the reactor was pressurized to 600 psig with hydrogen. The mixture was heated to 72° C. and the pressure allowed to drop to 300 psig at which time hydrogen was added to bring the pressure back to 600 psig. This process was repeated until hydrogen consumption had ceased. The reactor was allowed to cool to 30° C. and the contents were filtered to remove the catalyst. Removal of the solvent under reduced pressure afforded 100 g (96.9%) of farnesane dimers consisting of 15 isomeric compounds of molecular weight 420 (GC/MS). Celite on a 60 mL medium porosity sintered glass funnel to afford 200 g (98.3%) of clear colorless oil. The presence of compounds II-A, II-C, II-B, and II-D were confirmed by ¹H NMR.

¹H (400 MHz, CDCl₃) d (multiplicity, coupling constant{s}, integration*) 1.79-1.55 (m, 4.08H), 1.52 (m, J=6.8 Hz, 4.94H), 1.59-1.00 (m, 53.95H), 1.05, 0.87, 0.86, 0.85, 0.85, 0.83, 0.83, 0.82, 0.81, 0.80, 0.79 (s, 36.01 total H).

Farnesane 1,4-Dimer (90% pure): ¹H (400 MHz, CDCl₃) d (multiplicity, coupling constant{s}, integration*) 5.42 (m, 1H), 5.12 (m, 4H), 4.75 (m, 2H), 2.10 (m, 15H), 1.98 (m, 8H), 1.682 (s, 3H), 1.680 (s, 3H), 1.60 (s, 12H) ppm.

* Integration values are relative areas peak to peak and not absolute numbers of protons.

Example 3

Figure 2:
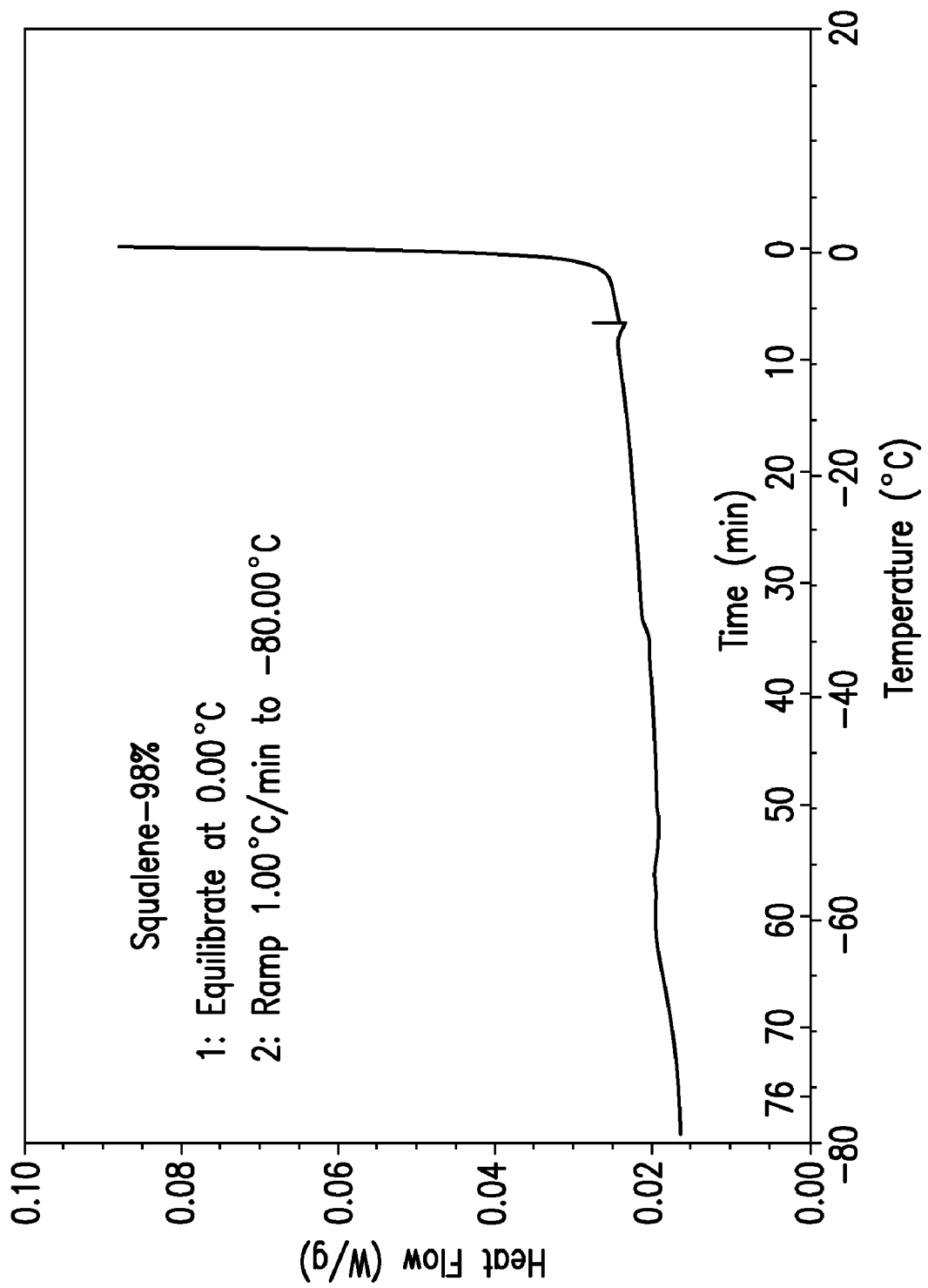
FIG. 2 depicts the DSC plot for compositions comprising 98% squalene.
Figure 3:
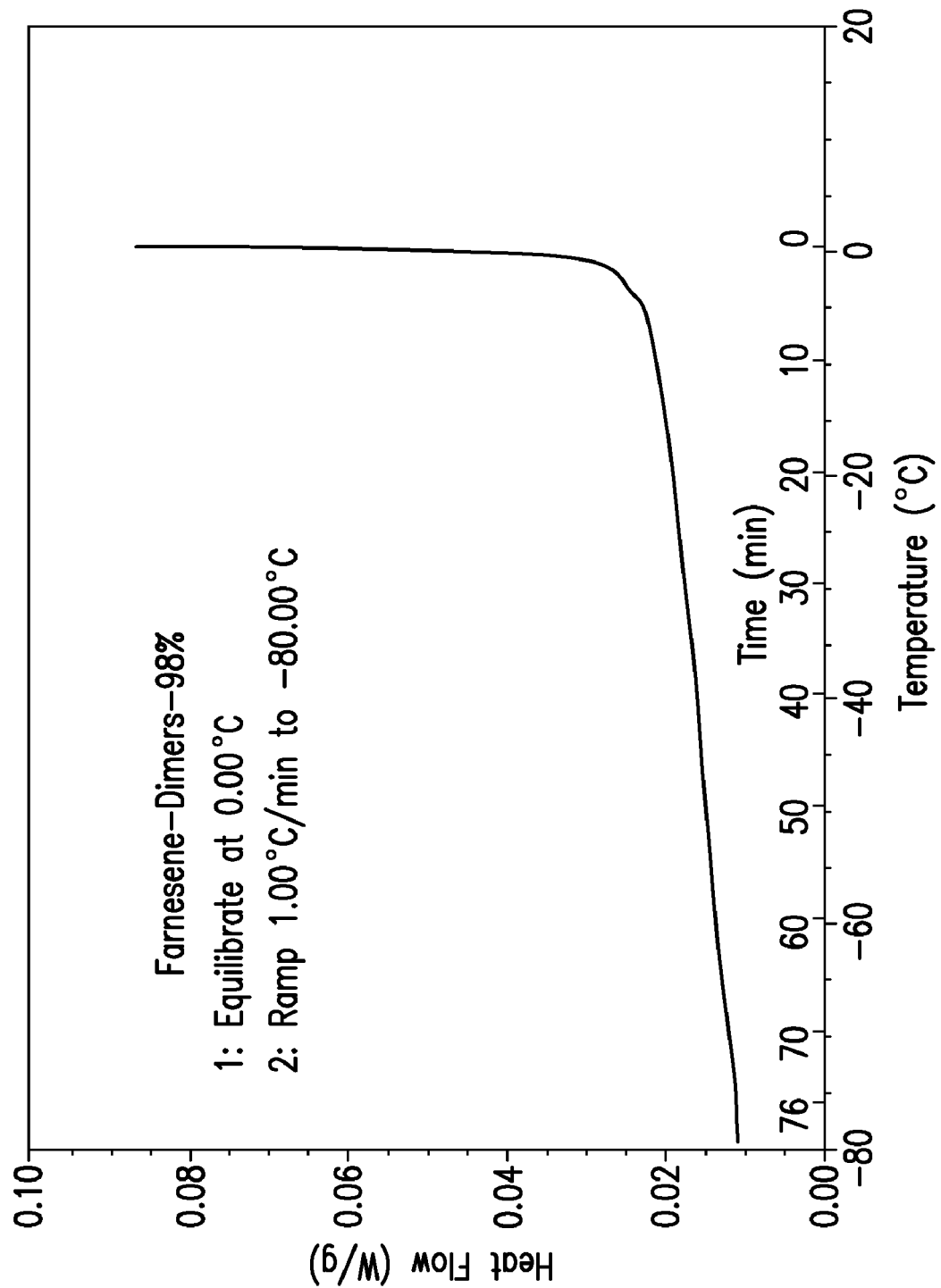
FIG. 3 depicts the DSC plot for compositions comprising 98% farnesene dimers.
Figure 4:
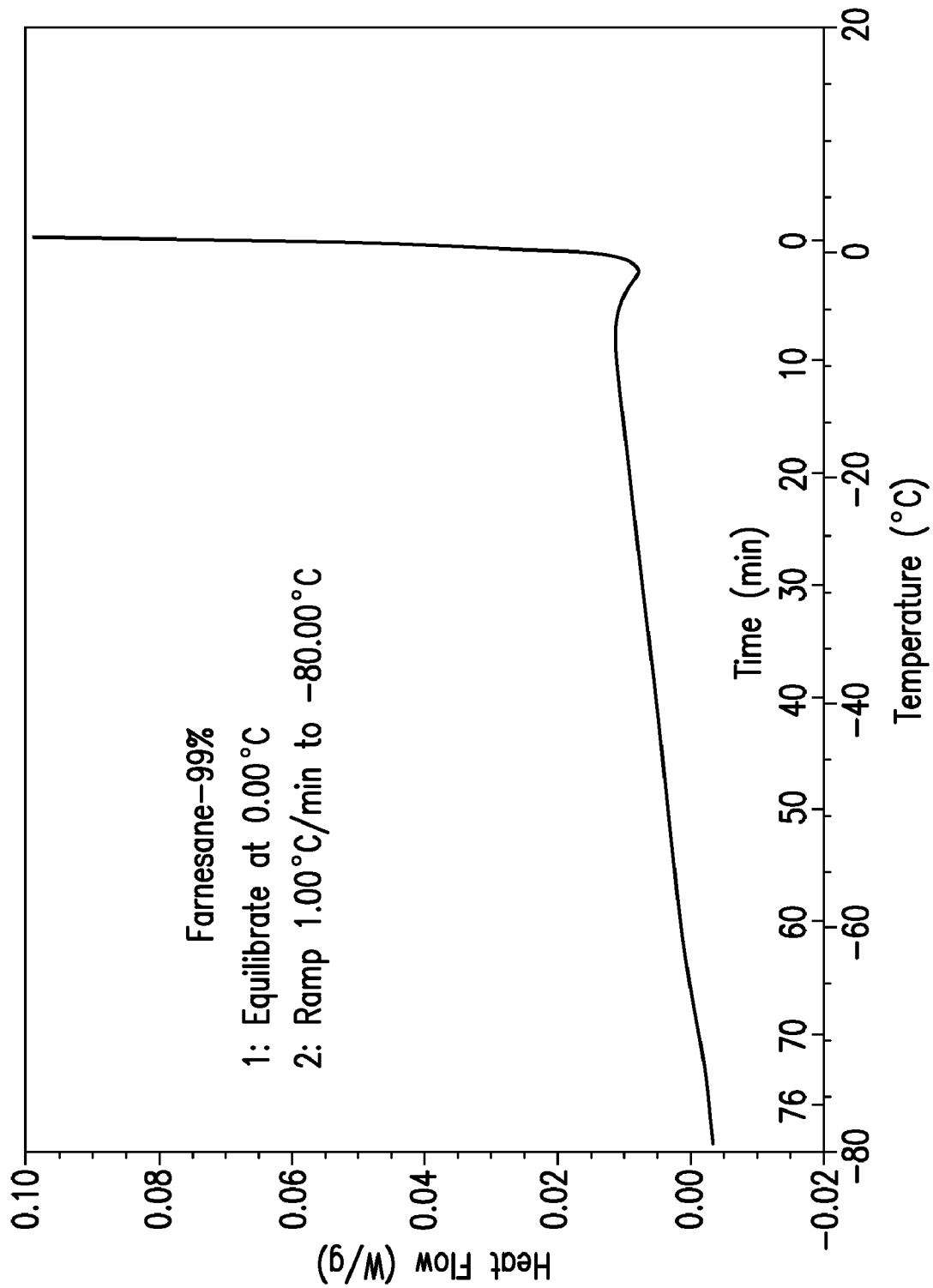
FIG. 4 depicts the DSC plot for compositions comprising 99% farnesane.

This example compares the compositions comprising farnesene dimers (98%), farnesane (99%), squalene (98%) and POA. Table 1 provides viscosity and viscosity index data for the 4 compositions. FIGS. 1-4 provide differential scanning calorimetry (DSC) plots for the compositions.

TABLE 1

|  | PAO | Squalene (98%) | Farnesene dimers (98%) | Farnesane (99%) | Farnesane dimers (98%) |
|---|---|---|---|---|---|
| CEC L-85-T-99 Oxidation Induction, min/ 210 0 C. | 0.69 | 0.17 | 0.02 | 1.42 | — |
| ASTM D-97 Pour Point, ° C. | <−60 | <−60 | <−60 | <−60 | −51 |
| ASTM D-445 Viscosity @ 40° C., cSt | 5.16 | 9.98 | 43.20 | 2.33 | 127.98 |
| ASTM D-445 Viscosity @ 100° C., cSt | 1.70 | 3.18 | 11.44 | 1.00 | 18.05 |

TABLE 1-continued

|  | PAO | Squalene (98%) | Farnesene dimers (98%) | Farnesane (99%) | Farnesane dimers (98%) |
|---|---|---|---|---|---|
| ASTM D-2270 Viscosity Index | * | 210 | 234 | * | 157 |
| ASTM D-4172 Four Ball Wear Test | — | 0.67 | 0.73 | — | — |
| Test Temperature, ° C., | 75 | 75 | 75 | 75 | — |
| Test Duration, hrs | 1 | 1 | 1 | 1 | — |
| Spindle Speed, rpm | 1200 | 1200 | 1200 | 1200 | — |
| Load, kg | 40 | 40 | 40 | 40 | — |
| Average Scar Diameter, mm | 0.96 | 0.67 | 0.73 | 0.96 | — |

* too low to calculate

Although the compositions comprising farnesene dimers have a high viscosity index (234 according to ASTM D-2270), the compositions are pourable liquids at room temperature.

Since modifications will be apparent to those of skill in the art, it is intended that the claimed subject matter be limited only by the scope of the appended claims.

What is claimed is:

1. A composition comprising:

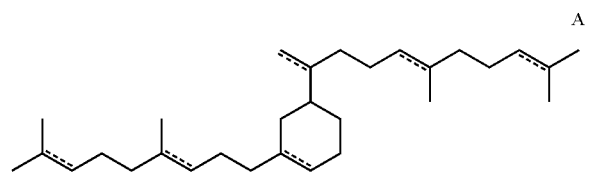

A and one or more compounds selected from:

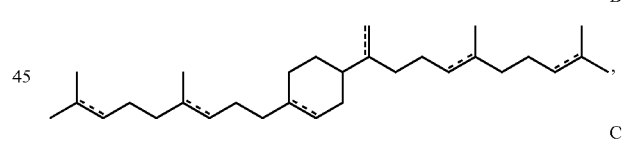

B

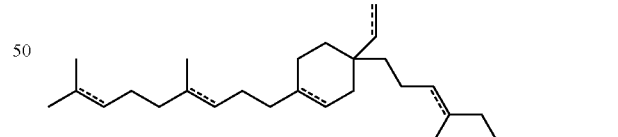

C

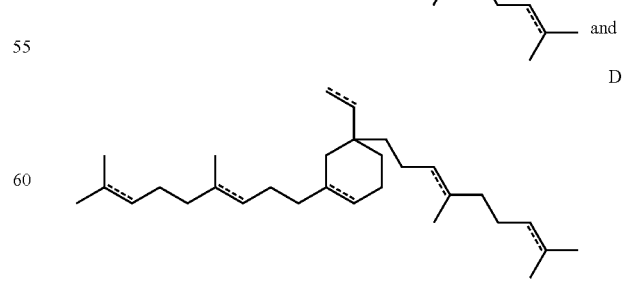

and

D wherein the dual lines indicate that each of compounds A, B, C, and D is either fully saturated or fully unsaturated.

2. The composition of claim 1, wherein compound A is

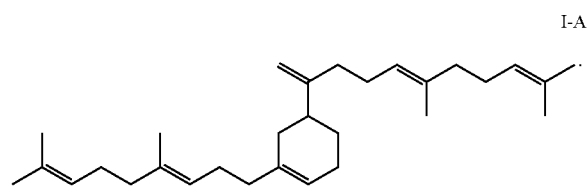

3. The composition of claim 1, wherein compound A is

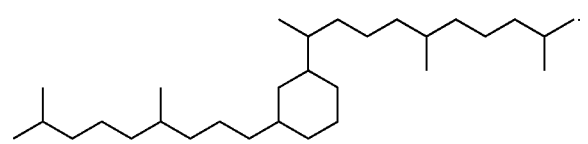

4. The composition of claim 1, wherein the one or more compounds are selected from:

5. The composition of claim 4 that comprises compounds I-A and 1-B, wherein compound I-A is

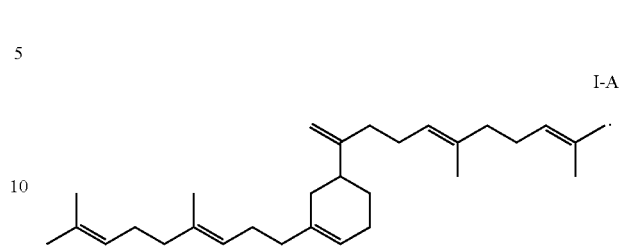

6. The composition of claim 5 that comprises at least about 20% compound I-A based on the total weight of the composition.

7. The composition of claim 5 that comprises at least about 20% compound I-B based on the total weight of the composition.

8. The composition of claim 5 further comprising at least about 2% compound I-C or at least about 2% compound I-D based on the total weight of the composition.

9. The composition of claim 4 that comprises about 10% compound I-A, about 10% compound I-B, about 1% com-

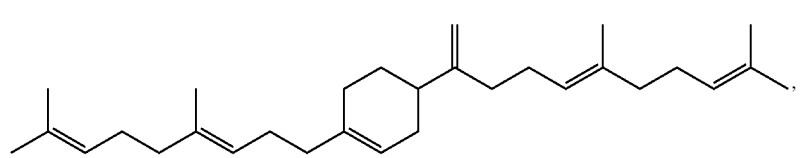

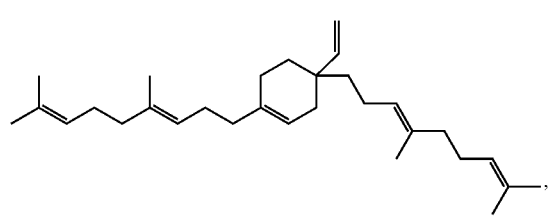

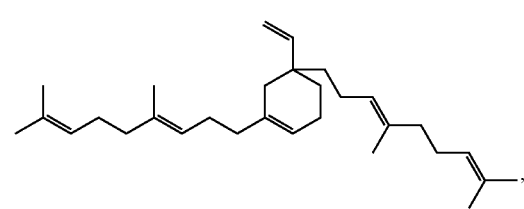

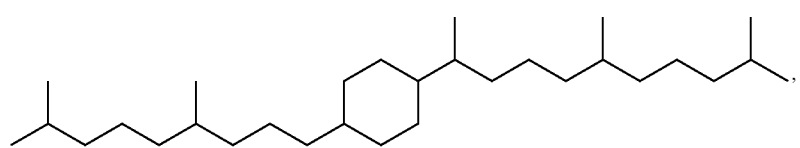

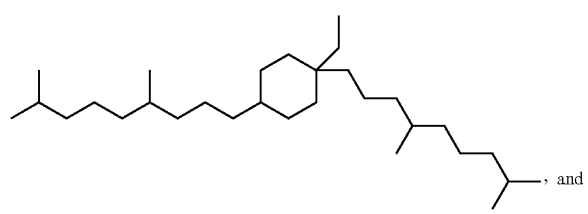

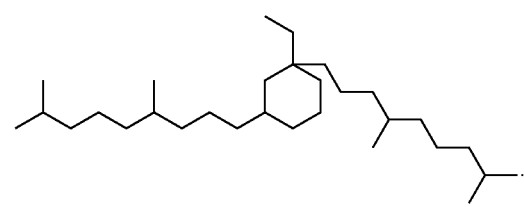

pound I-C and about 1% compound I-D based on the total weight of the composition, wherein compound I-A is

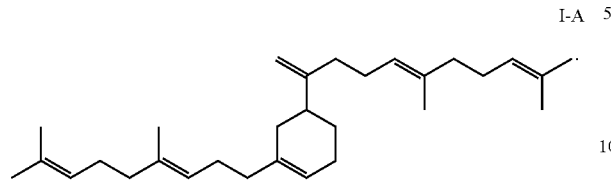

I-A

10. The composition of claim 9 that comprises about 20% compound I-A, about 20% compound I-B, about 2% compound I-C and about 2% compound I-D based on the total weight of the composition.

11. The composition of claim 4 that comprises compounds II-A and II-B, wherein compound II-A is

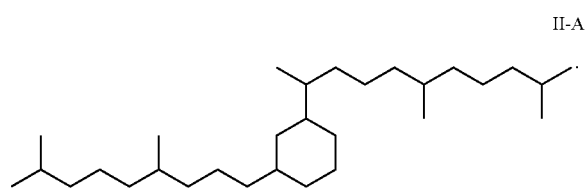

II-A

12. The composition of claim 11 that comprises at least about 20% compound II-A based on the total weight of the composition.

13. The composition of claim 11 that comprises at least about 20% compound II-B based on the total weight of the composition.

14. The composition of claim 4 comprising about 20% compound II-A, about 20% compound II-B, about 2% compound II-C and about 2% compound II-D based on the total weight of the composition, wherein compound II-A is

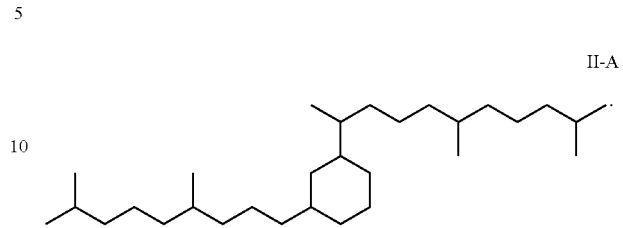

II-A

15. The composition of claim 1 that has viscosity of 5 cSt or 15 cSt at 100° C.

16. The composition of claim 1 that has a viscosity index of about 220 to about 245 according to ASTM D 2270.

17. The composition of claim 1 that is a lubricant composition.

18. The composition of claim 1 further comprising at least one additive selected from the group consisting of an antioxidant, an antiwear agent, a detergent, a rust inhibitor, a demulsifier, a friction modifier, a multi-functional additive, a viscosity index improver, a pour point depressant, a foam inhibitor, a metal deactivator, a dispersant, a corrosion inhibitor, a lubricity improver, a solubilizing agent, a seal-swell agent and combinations thereof.

19. A method of lubricating a machine comprising the step of operating the machine in contact with the composition of claim 1.

20. A machine comprising the composition of claim 1, wherein the composition is used to lubricate the machine.

* * * * *